(12) United States Patent
Hu

(10) Patent No.: US 8,718,345 B2
(45) Date of Patent: May 6, 2014

(54) METHOD AND SYSTEM FOR OBTAINING BRAIN CHARACTERISTIC PARAMETERS, THROMBOLYSIS DECISION GUIDELINE SYSTEM AND METHOD THEREOF

(75) Inventor: Qingmao Hu, Guangdong (CN)

(73) Assignee: Shengzhen Institutes of Advanced Technology Chinese Academy of Sciences, Guangdong (CN)

( * ) Notice: Subject to any disclaimer, the term of this patent is extended or adjusted under 35 U.S.C. 154(b) by 231 days.

(21) Appl. No.: 13/376,943

(22) PCT Filed: Jun. 16, 2009

(86) PCT No.: PCT/CN2009/072305
§ 371 (c)(1),
(2), (4) Date: Dec. 8, 2011

(87) PCT Pub. No.: WO2010/142085
PCT Pub. Date: Dec. 16, 2010

(65) Prior Publication Data
US 2012/0076387 A1    Mar. 29, 2012

(30) Foreign Application Priority Data

Jun. 12, 2009    (CN) .......................... 2009 1 0107936

(51) Int. Cl.
*G06K 9/00*    (2006.01)
(52) U.S. Cl.
USPC ....................................................... 382/131

(58) Field of Classification Search
None
See application file for complete search history.

(56) References Cited

U.S. PATENT DOCUMENTS

2004/0138549 A1* 7/2004 Wintermark et al. ......... 600/407
2009/0034812 A1* 2/2009 Nowinski et al. ............. 382/131

OTHER PUBLICATIONS

Rohl, L. et al., "Viability Thresholds of Ischemic Penumbra of Hyperacute Stroke Defined by Perfusion-Weighted MRI and Apparent Diffusion Coefficient," Journal of the American Heart Association, May 2001, 8 pages.*

* cited by examiner

Primary Examiner — Jason M Repko
Assistant Examiner — Ryan P Potts
(74) Attorney, Agent, or Firm — Rosenberg, Klein & Lee

(57) ABSTRACT

Method and system for obtaining brain characteristic parameters, thrombolysis decision guideline system and method thereof, provide middle of reference data for early diagnosis and treatment of acute ischemic brain death, and provide effective reference data for thrombolytic therapy. The present invention uses diffusion-weighted imaging, comparing to the clinical programs of diffusion-weighted imaging and perfusion weighted imaging, perfusion weighted imaging can omitted and the degree of functional characterization of perfusion abnormalities is reflected without the perfusion weighted imaging, to provide middle data of brain tissue can be saved and the risk of thrombolytic therapy. The present invention based on ADC low signal constraint and DWI high signal constraint DWI binarization processing to obtain the core area and transition area, that is more accurate.

29 Claims, 12 Drawing Sheets

METHOD AND SYSTEM FOR OBTAINING BRAIN CHARACTERISTIC PARAMETERS, THROMBOLYSIS DECISION GUIDELINE SYSTEM AND METHOD THEREOF

FIELD OF THE INVENTION

The present disclosure relates to medical imaging technology, and more particularly relates to a method for obtaining brain characteristic parameters by using magnetic resonance imaging.

The present invention further relates to a system for obtaining brain characteristic parameters by using magnetic resonance imaging.

The present invention further relates to a method for thrombolysis decision guideline by using magnetic resonance imaging.

The present invention further relates to a system for thrombolysis decision guideline by using magnetic resonance imaging.

BACKGROUND OF THE INVENTION

Cerebrovascular disease increased gradually in recent years, and is a second disease in cause of death in China that found by epidemiological researcher. In China, there are 1.3 to 1.5 million of new cerebrovascular disease cases, 6 to 7 million of the total number of sick people, while people died from cerebrovascular disease are nearly 1 million each year, about ¾ of the survivors of are different degrees of incapacity, severe disability in 40% or more. The cerebrovascular disease has a higher morbidity, and is serious harm to human health and quality of life, which result in social and economic of hospitals, physicians, rehabilitation, pharmacy, and indirect consumption of up to 30 billion yuan per year. People dying from the ischemic stroke (cerebral infarction) disease accounts for 70% of the people that died from cerebrovascular disease, therefore, the study of cerebral infarction is very important.

Every state guideline recommends that the ischemic stroke in the ultra-super-early (within 3 hours) is preferredly healed by thrombolytic therapy of intravenous recombinant tissue-type plasminogen activator (rt-PA). However, the number of patients with ischemic stroke healed by hyperacute thrombolytic therapy is less than 1% in China. According to statistics, patients of hyperacute ischemic healed by rt-PA treatment are only 409 of the whole of China in 2004. Compared to newly issued 1.3 million of patients with ischemic stroke, the number of patients of hyperacute ischemic healed by rt-PA treatment is undoubtedly shocking. In the United States, there are at least 0.7 million new cases of ischemic stroke, but only 1% can be healed by thrombolytic therapy. This phenomenon is largely caused by that thrombolytic therapy is prone to bring other serious complications. Therefore, patients must be cured strictly in accordance with pathological state of the brain. However, how to understand the pathological state of patient is a difficulty of medicine, which is difficult to overcome.

For a long time, how to make the early diagnosis of ischemic stroke, determination of ischemic penumbra and effective implement for cerebral protection, saving of the damaged nerve function of the ischemic penumbra, have been the main treatment direction for ischemic stroke. Astrup J. et al present a concept of ischemic penumbra guides in 1981. The theory of ischemic penumbra guides shows that cerebral ischemia induces existence of a central necrosis area and a penumbra area surrounding the central necrosis area. The penumbra area losses neurological function, but nerve cells of the penumbra are still alive. At this point, if reperfusion active thrombolytic treatment is valid in a time window, most brain cells still prevent ischemic necrosis. The main purpose of thrombolysis is to save the ischemic penumbra area, restore tissue blood supply, and improve clinical symptoms. Therefore, presence of the ischemic penumbra area is a basic condition for thrombolytic therapy.

The ischemic penumbra and the central necrosis are a dynamic process of the pathophysiology, which is closely related to ischemia time, vascular occlusion and collateral circulation. With aggravation of ischemia and prolonged ischemia time, the central necrotic area is gradually expanded, the ischemic penumbra area is gradually shrunk. Therefore, the time window of reperfusion of the thrombolytic therapy is strict, over the time window of reperfusion may aggravate cerebral edema and brain cell damage, and increase mortality. A study researched by Absett et al shows that continuous treatment of 400 patients in 6 hours time window, the number of patients cured within 3 hours is only 10%, the number of patients cured within 3-6 hours is accounted for 90% of all cases, the number of patients cured within 5-6 hours is also accounted for 50% of all cases. Therefore, within the super-acute phase which is called the "time is brain", the number of patients benefited from thrombolytic therapy will grow exponentially at each extended hour. Thrombolytic therapy determines whether the ischemic penumbra area is existed and whether vascular barrier through the guidance of imaging damaged, and is no longer calculated in accordance with the onset of reperfusion time window, which extends the reperfusion time window and increase the number of patients accepted thrombolytic therapy. Practice of medicine shows that the radiographic can recognize the ischemic penumbra area to guide clinical treatment, and obtain satisfactory results in the traditional treatment time window. By the radiographic guidance, ten thousands of patients of peracute ischemic stroke can benefit from the thrombolytic therapy each year.

At present, the ischemic penumbra area is determined by a combination of magnetic resonance diffusion weighted imaging and magnetic resonance perfusion weighted imaging. The diffusion weighted imaging is referred to as DWI. The perfusion weighted imaging is referred to PWI. High signal abnormal area of the diffusion weighted imaging (DWI) represents a cerebral infarction area. Perfusion abnormal area of the PWI represents a damaged area. A unmatch area between the PWI and the DWI is a possible ischemic penumbra area, which is defined the difference between the perfusion abnormal area of the PWI and the high signal abnormal area of the DWI. PWI>DWI is considered as the best way of clinical thrombolysis guideline.

However, the above model has the following serious shortcomings:

(1) The PWI requires injection of contrast agent, which is a relative measurement because different scanning machines have no uniform standard.

(2) The perfusion abnormal area of the PWI in accordance with qualitative analysis, and calculation time of the perfusion abnormal area is rather time-consuming. Furthermore, this brain flow model is still controversial, and the magnetic resonance perfusion weighted imaging do not pass the U.S. Food and Drug Administration (FDA) approval, such that this brain flow model may be have a clinical risk.

(3) The DWI is not only dependent on the dispersion characteristics, but also on the a T1 weighted, a T2 weighted and a proton density, especially on the T2-weighted.

(4) The actual ischemic penumbra area is usually smaller than the unmatch area of PWI/DWI. An error between the actual ischemic penumbra area and the unmatch area is up to 40%-60%.

(5) A difficulty of determining the infarction area, the ischemic penumbra area by PWI/DWI is a significantly different of diffusion and perfusion characteristics of different brain tissue (gray matter and white matter). The significantly difference can be up to 20%. If the significantly difference does not distinguish, there will be bring principle error.

In view of inherent weaknesses of the PWI and unmatch difficulty of the PWI/DWI, Prosser et al. advance a ischemic penumbra band model of clinical unmatch in accordance with the DWI, but the ischemic penumbra band model of clinical unmatch can be only achieved 53% of sensitivity.

Therefore, a method and system for obtaining brain characteristic parameters, a thrombolysis decision guideline system and method thereof are desired in order to overcome the above-described shortcomings.

SUMMARY OF THE INVENTION

It is an object of the present disclosure to provide a method for obtaining brain characteristic parameters. The method for obtaining brain characteristic parameters includes:

step S1, selecting a magnetic resonance perfusion weighted imaging of a patient obtained in accordance with magnetic resonance, wherein the magnetic resonance perfusion weighted imaging includes a Diffusion-weighted image, T2-weighted image, and an apparent diffusion coefficient map;

step S2, distinguishing a brain tissue from a non-brain tissue in accordance with the T2-weighted image, and obtaining a brain tissue image without the non-brain tissue;

step S3, processing voxels of the ADC map corresponding to the brain tissue image in accordance with low ADC signal constraint binarizing to obtain a binary image according to calculated ADC thresholds of a transition area;

step S4, estimating core area and transition area according to the binary image and ADC thresholds of the core area in accordance with calculating;

step S5, processing the estimated core area according to high signal constraint processing in accordance with high thresholds of the DWI of the estimated core area, and obtaining the core area and the transition area; and step S6, calculating characteristic parameters of the core area and the transition area.

In a preferred embodiment, the method for obtaining brain characteristic parameters further includes step S11: converting input image data of the DWI to lower bit image data, between step S1 and step S2.

In a preferred embodiment, step S2 includes:
step S21, obtaining a low signal threshold of the brain tissue by dividing the T2-weighted image into fuzzy C-means clustering;
step S22, binarizating the T2-weighted image in accordance with the low signal threshold to obtain the binary image; if gray of one pixel of the T2-weighted image is no less than the low signal threshold, set the pixel to foreground; if not, set the pixel to background;
step S23, obtaining the largest connected area of the binary image; and
step S24, opening slices of the largest connected area in the mathematical morphology, determining the biggest foreground connected area and obtaining a brain image by filling in the slices of the largest connected area.

In a preferred embodiment, step S3 and step S4 include:
step S31, determining an ADC value of normal brain tissue of the brain image based on the ADC map; and
step S32, calculating a product between the ADC value of the normal brain tissue and a threshold coefficient, and obtaining ADC threshold of the core area and ADC threshold of the transition area.

In a preferred embodiment, step S31 includes:
step S311, counting occurrence times of each ADC value of the ADC map corresponding to the brain tissue image; and
step S312, determining the ADC value of the normal brain tissue by the counting result, wherein the ADC value of the normal brain tissue is any value in neighborhood scope of the ADC value of the highest occurrence times.

In a preferred embodiment, the ADC value of the normal brain tissue is any value in neighborhood scope of the most frequent of ADC values in step S31; the ADC thresholds of the core area and the ADC thresholds the transition area are calculated based on the ADC value of the normal brain tissue in step S32; each slice of the brain tissue image is binarized based on the ADC thresholds of the transition area in step S3; the core area and the transition area are estimated based on the binary image of the each slice in step S4; the core area and the transition area are obtained by high signal constraint processing of the binary image of the each slice in step S5; characteristic parameters of the core area and the transition area is calculated in step S6.

In a preferred embodiment, step S3 further includes: if an ADC value of a pixel is greater than the ADC threshold of the transition area, the pixel is a background pixel; if not, the pixel is a foreground pixel.

In a preferred embodiment, step S4 includes:
step S41, obtaining a foreground connected area in accordance with the binary image of the ADC map; and
step S42, dividing the foreground connected area into a foreground area and a background area to obtain a first image, wherein if the volume of the foreground connected area is not less than the volume of the first pre-volume, and a voxel of the foreground connected area of which ADC value is less than the ADC threshold of the core area is not less than the second pre-volume, the foreground connected area is a foreground; if not, the foreground connected area is a background.

In a preferred embodiment, step S5 includes:
denoting the mean gray scale value of the DWI of the core area to DWIAvgF;
denoting the DWI gray scale value of all voxels adjacent to the core area to DWIAvgB;
selecting all voxels of brain tissue of which the DWI gray scale value is no less than a constant, and denoting mean gray scale and standard deviation of the voxels for the DWI and the to AvgDWI(z) and SdDWI(z);
denoting the high signal threshold of the DWI to DWITh(z), and calculating the high signal constraint of the DWI by the following formulas:

$$DWITh(z)=AvgDWI(z)+CC1*SdDWI(z),$$

wherein CC1 represents a constant, * represents multiplication; and
wherein if (DWIAvgF−DWIAvgB)>CC2 or (DWIAvgF−DWITh(z))>CC3, the core area and the transition area are retained; if not, the core area and the transition area are background; wherein CC2 and CC3 represents constants.

In a preferred embodiment, CC1 is a range from about 1.1 to about 1.5, CC2 is a range from about 10 to about 20, and CC3 is a range from about 4 to about 8.

In a preferred embodiment, The method for obtaining brain characteristic parameters further includes: a recovering step between step S5 and step S6, and the recovering step comprising: setting the voxel of which ADC value is no greater than the ADC threshold of the transition area as the foreground voxel, and finding the adjacent voxels of each foreground voxel of the first image.

In a preferred embodiment, the method for obtaining brain characteristic parameters further includes: a second artifact removing step between the recovering step and step S6, and the second artifact removing step comprising: setting partial area of the foreground connected area of which volume is less than a preset volume as the background area, and finding the foreground connected area of the first image.

In a preferred embodiment, step S6 includes:
defining an core area and an transition area, the core area is a set of voxels of which ADC value is less than the ADC threshold of the core area, and the transition area is a set of voxels of which ADC value between the ADC threshold of the core area and the ADC threshold of the transition area; finding at least one connected area having the most foreground voxel of the core area and the transition area, and calculating characteristic parameters of the core area and the transition area in accordance with the connected area.

In a preferred embodiment, step S6 includes:
step S61, calculating an ADC value gradient of the transition area, wherein step S61 includes:
step S611, finding a connected area having the largest foreground voxels;
step S612, finding interior points of the connected area;
step S613, calculating a mean ADC value gradient of interior points of which ADC value between the ADC threshold of the core area and the ADC threshold of the transition area;
step S614, calculating a mean ADC value of voxels of which ADC value between the ADC threshold of the core area and the ADC threshold of the transition area; and
step S615, calculating an ADC value gradient of the transition area by the following formula:

$$gradAvgN = gradAvg \times C/(ADC_{ref} \times avgADC);$$

wherein gradAvgN represents the ADC value gradient of the transition area, gradAvg represents the mean ADC value gradient of the connected area in step S613, C represents a positive constant, $ADC_{ref}$ represents ADC value of the normal brain tissue, and avgADC represents the mean ADC value gradient in step S614; step S62, calculating a radial distance of the transition area, wherein step S62 includes:
step S621, calculating the number of first voxels of the connected area of which ADC value is less than the ADC threshold of the core area, and the number of second voxels of the connected area of which ADC value between the ADC threshold of the core area and the ADC threshold of the transition area;
step S622, calculating a radius of the core area of the connected area and a radius of the core area and the transition area of the connected area respectively, wherein the radius of the core area is square root of a quotient© which is calculated by dividing the number of the first voxels to pi and the radius of the transition area is square root of a quotient which is calculated by dividing the sum of the number of the first voxels and the number of the second voxels to pi; and
step S623, calculating a radial distance of the transition area by minusing the radius of the core area and the radius of the transition area.

In a preferred embodiment, step S6 further includes step S63: calculating a total change of radial ADC value of the transition area by the following formulas:

$$\delta ADC = gradAvgN \times \delta R/ADC_{ref};$$

wherein $\delta ADC$ is a total change of ADC, gradAvgN represents the gradient of ADC value of the transition area, $\delta R$ represents the radial distance of the transition area, and $ADC_{ref}$ represents ADC value of the normal brain tissue.

In a preferred embodiment, step S6 further includes step S64: calculating a variation coefficient of ADC value of the core area; wherein step S64 includes:
step S641, calculating a mean ADC value and a mean square errors of voxels of which ADC value is less than the ADC threshold of the core area;
step S642, dividing the mean ADC value by the mean square errors, and the variation coefficient of ADC value of the connected area is equal to the quotient.

In a preferred embodiment, step S6 further includes:
step S65, calculating parameters of partial edge area of the core area adjacent to the transition area and a mean ADC value of voxels of all core area and a mean square errors of voxels of all core area, and denoting the mean ADC value and the mean square errors to $AvgADC_{core}$ and $SdACD_{core}$; eroding the core area by 3×3 mathematical morphology erosion, and denoting a mean ADC value and a mean square errors of the remaining core area to $AvgADC_{coreE}$ and $SdACD_{coreE}$; calculating the change of the mean ADC value of partial edge area of the core area adjacent to the transition area by the following formulas:

$$\delta AvgADC = (AvgADC_{core} - AvgADC_{coreE})/AvgADC_{core};$$

calculating the change of the mean square errors of ADC value of partial edge area of the core area adjacent to the transition area by the following formulas:

$$\delta SdADC = (SdADC_{core} - SdADC_{coreE})/SdADC_{core};$$

calculating the change of the variation coefficient of ADC value of partial edge area of the core area adjacent to the transition area by the following formulas:

$$\delta CvADC = \delta SdADC/\delta AvgADC.$$

In a preferred embodiment, step S6 further includes: selecting a first and second connected area and obtaining characteristic parameters of the first and second connected area; comparing the characteristic parameters of the first connected area to that of the second connected area, and outputting the minimum characteristic parameters or the maximum characteristic parameters.

It is another object to provide a system for obtaining brain characteristic parameters. The system for obtaining brain characteristic parameters includes:
an inputting device, configured to obtain a magnetic resonance perfusion weighted imaging of a patient obtained in accordance with magnetic resonance, wherein the magnetic resonance perfusion weighted imaging includes a DWI, T2-weighted image, and an ADC map;
a brain tissue extracting module, configured to calculate a brain tissue of patient in accordance with the T2-weighted image, and output a brain image;
an image processing module, configured to obtain a binary image based on binarizing the voxels of the ADC map corresponding to the brain tissue image in accordance with low ADC signal constraint binarizing according to ADC thresholds of a transition area in accordance with calculating; and estimate core area and transition area according to the binary image and ADC thresholds of a core area in accordance with calculating; and process the core area obtained by estimating in accordance with high signal constraint processing according to DWI high signal thresholds of the core area in accordance with estimating, and obtaining the core and the transition area; and a characteristic parameters calculating unit, configured to calculate characteristic parameters of the core area and the transition area.

In a preferred embodiment, the inputting device includes a data processing unit configured to convert data of the DWI, the T2-weighted image, and the ADC map to a lower bit data, wherein an output end of the data processing unit is connected to the image processing module and the brain tissue extracting module.

In a preferred embodiment, the image processing module includes:
a normal ADC value obtaining module, configured to obtain ADC values of a normal brain tissue, wherein the normal ADC values of obtaining module is connected to the brain tissue extracting module and the outputting device;
an ADC low signal thresholds calculating module, configured to calculate a product between the ADC value of the normal brain tissue and a threshold coefficient, and obtain an ADC threshold of the core area and the transition area;
an DWI high signal thresholds calculating module, configured to select all voxels of brain tissue of which the DWI gray scale is no less than a constant, and denoting mean gray scale and standard deviation of the voxels for the DWI and the to AvgDWI(z) and SdDWI(z); denoting the high signal threshold of the DWI to DWITh(z), and calculate the high signal constraint of the DWI by the following formulas:

$$DWITh(z) = AvgDWI(z) + CC1 * SdDWI(z),$$

wherein CC1 represents a constant, * represents multiplication;
a low signal constraint binarizing module, configured to obtain a binary image based on binarizing the ADC map in accordance with ADC low signal constraint binarizing according to the ADC thresholds of the transition area, wherein the low signal constraint binarizing module is connected to the inputting device, the brain tissue extracting module and the ADC low signal thresholds calculating module;
an estimating unit, configured to estimate core area and transition area in accordance with the binary image, wherein the estimating unit is connected to the low signal constraint binarizing module and the ADC low signal thresholds calculating module;
a high signal constraint processing unit, configured to process the core area in accordance with high signal constraint processing according to ADC high signal thresholds of the core area in accordance with estimating, wherein the high signal constraint processing unit is connected to the estimating unit and the DWI high signal thresholds calculating module;
a determination unit, configured to define an core area and an transition area, wherein the core area is a set of voxels of which ADC value is less than the ADC threshold of the core area, and the transition area is a set of voxels of which ADC value between the ADC threshold of the core area;
a characteristic parameter calculating unit, configured to find at least one connected area having the largest voxels in the core area and the transition area, and calculate characteristic parameters of the core area and the transition area, wherein the characteristic parameter calculating unit is connected to the determination unit.

In a preferred embodiment, the high signal constraint processing unit is configured to:
denote the mean gray scale of the DWI of the core area to DWIAvgF;
denote the DWI gray scale of all voxels adjacent to the core area to DWIAvgB;
denote the high signal threshold of the DWI to DWITh(z);

wherein if (DWIAvgF−DWIAvgB)>CC2 or (DWIAvgF−DWITh(z))>CC3, the core area and the transition area is retained; if not, the core area and the transition area is background; wherein CC2 and CC3 represents constants.

In a preferred embodiment, the estimating unit includes:
a first unit, configured to obtain a foreground connected area of each slice of the brain tissue in accordance with the binary image;
a first artifact removing unit, configured to obtain a foreground area, the foreground area is a part of the foreground connected area of which volume is greater than or equal to a first preset volume, and includes at least one voxel of which volume is greater than or equal to a second preset volume, and of which ADC value is less than the ADC threshold of the core area, the other part of the foreground connected area excluding the foreground area is the background area.

In a preferred embodiment, the image processing module further includes:
a recovering unit, configured to set the voxel of which ADC value is no greater than the ADC threshold of the transition area as the foreground voxel, and find the adjacent voxels of each foreground voxel, wherein the recovering unit is connected between the high signal constraint processing unit and the determination unit.

In a preferred embodiment, the image processing module further includes:
a second artifact removing unit, configured to set partial area of the foreground connected area of which volume is less than a preset volume as the background area, and finding the foreground connected area, wherein the second artifact removing unit is connected between the recovering unit and the determination unit.

It is another object to provide a thrombolysis decision guideline system. The thrombolysis decision guideline system includes:
an inputting device, configured to obtain a magnetic resonance perfusion weighted imaging of a patient obtained in accordance with magnetic resonance, wherein the magnetic resonance perfusion weighted imaging includes a DWI, T2-weighted image, and an ADC map;
a brain tissue extracting module, configured to calculate a brain tissue of patient in accordance with the T2-weighted image, and output a brain image;
an image processing module, configured to obtain a binary image based on binarizing the voxels of the ADC map corresponding to the brain tissue image in accordance with ADC low signal constraint binarizing according to ADC thresholds of a transition area in accordance with calculating; and estimate core area and transition area according to the binary image and ADC thresholds of a core area in accordance with calculating; and process the core area obtained by estimating in accordance with high signal constraint processing according to DWI high signal thresholds of the core area in accordance with estimating, and obtaining the core and the transition area;
a characteristic parameters calculating unit, configured to calculate characteristic parameters of the core area and the transition area;
a training database, configured to store a preset threshold of the core area and the transition area; and
a determination unit, configured to compare output characteristic parameters of the characteristic parameters calculating unit to the preset threshold and output a comparison result.

In a preferred embodiment, the preset threshold of the training database includes a limiting value of variation coefficient of ADC value of the core area, a total change of radial ADC value gradient of the transition area, volume of the core area, volume ratio of the core area and the transition area, a mean ADC value of partial edge area of the core area adjacent to the transition area, a change of the mean square errors of ADC value, and a change of the variation coefficient of ADC value.

It is another object to provide a method of thrombolysis decision. The method of thrombolysis decision includes:

step S1, selecting a magnetic resonance perfusion weighted imaging of a patient obtained in accordance with magnetic resonance, wherein the magnetic resonance perfusion weighted imaging includes a DWI, T2-weighted image, and an ADC map;

step S2, distinguishing a brain tissue from a non-brain tissue in accordance with the T2-weighted image, and obtaining a brain tissue image without the non-brain tissue;

step S3, binarizing voxels of the ADC map corresponding to the brain tissue image in accordance with ADC low signal constraint binarizing to obtain a binary image according to ADC thresholds of a transition area in accordance with calculating;

step S4, estimating core area and transition area according to the binary image and ADC thresholds of the core area in accordance with calculating;

step S5, processing the core area obtained by estimating in accordance with high signal constraint processing according to DWI high signal thresholds of the core area in accordance with estimating, and obtaining the core and the transition area;

step S6, calculating characteristic parameters of the core area and the transition area; and step S7, comparing output characteristic parameters to a preset threshold and output a comparison result.

In a preferred embodiment, step S7 includes: obtaining the preset threshold based on comparing and training at least one parameter of a radial distance of the transition area, an ADC value gradient of the transition area, a total change of ADC value gradient of the transition area, a mean ADC value of the core area, a variation coefficient of ADC value of the core area, volume of the core area, volume ratio of the core area and the transition area, a mean ADC value of partial edge area of the core area adjacent to the transition area, a change of the mean square errors of ADC value, and a change of the variation coefficient of ADC value.

Comparing to the clinical programs of DWI and PWI, the present disclosure has the following advantages: the PWI can also be omitted, and the degree of functional characterization of perfusion abnormalities is reflected without the PWI. Therefore, cost and time of treatment of patient can be saved. In addition, the thrombolysis whether is implemented can be determined more accurately. Therefore, suffering and economic burden of the patient can be reduced.

Other advantages and novel features will become more apparent from the following detailed description of various embodiments, when taken in conjunction with the accompanying drawings.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout several views, and all the views are schematic.

DETAILED DESCRIPTION OF THE EMBODIMENTS

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Embodiment 1

Figure 1:
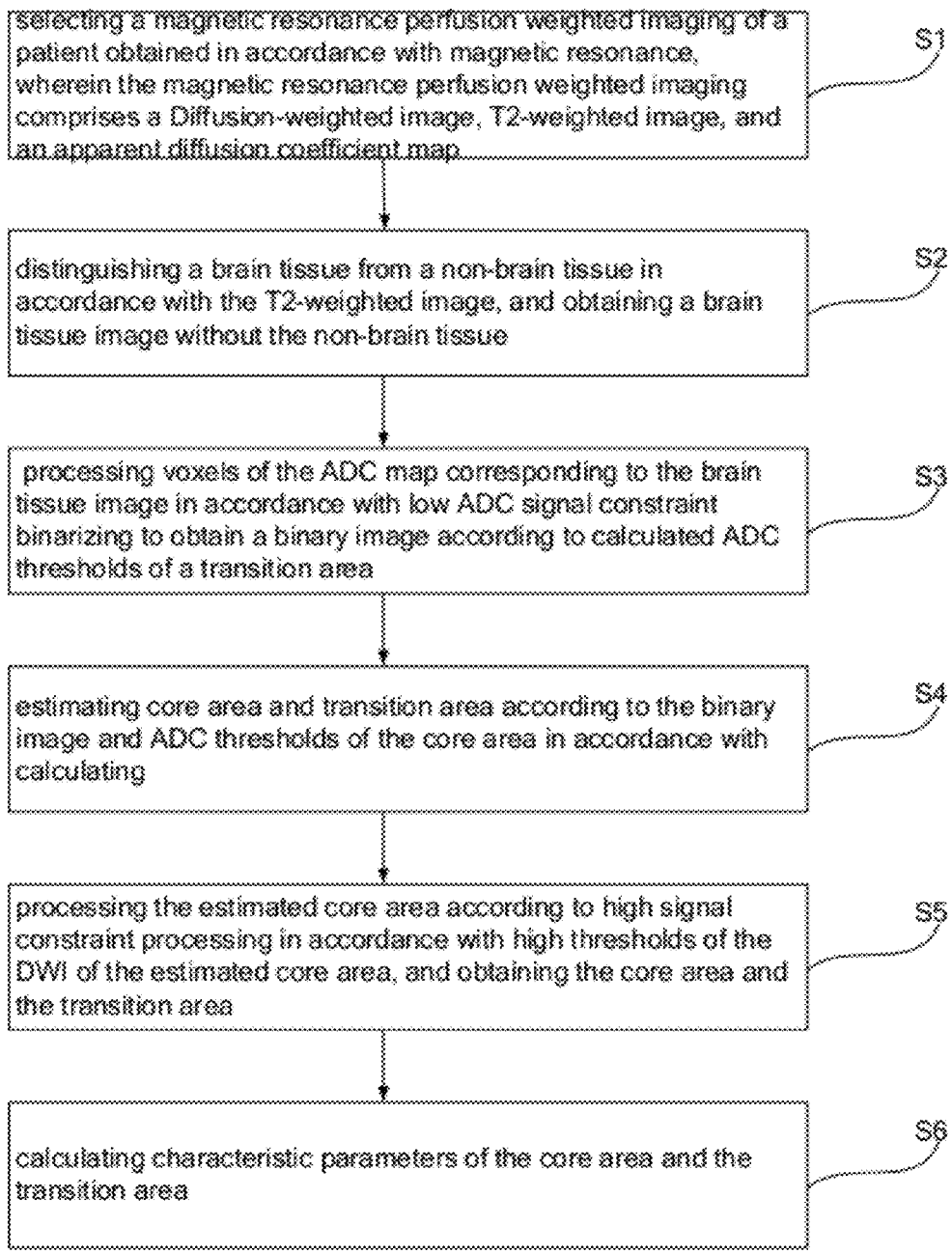
FIG. 1 is a flowchart of one embodiment of a method for obtaining brain characteristic parameters.

Referring to FIG. 1, a method for obtaining brain characteristic parameters according to a preferred embodiment is used to estimate a cerebral infarction area and an ischemic penumbra area of patient, and analysis characteristic parameters of the cerebral infarction area and the ischemic penumbra area. According to the method for obtaining brain characteristic parameters, reclaimable organizations find a method of analyzing risks of thrombolytic therapy. A core area of the present disclosure represents to the cerebral infarction area. A transition area of the present disclosure represents an area whose ischemic degree between that of the cerebral infarction area and a normal tissue area. The transition area is an estimate of the ischemic penumbra area. The method for obtaining brain characteristic parameters includes the following steps:

In step S1, a magnetic resonance perfusion weighted imaging of a patient obtained in accordance with magnetic resonance is selected, wherein the magnetic resonance perfusion weighted imaging includes a Diffusion-weighted image of which a diffusion sensitivity factor b=0, T2-weighted image of which an isotropic diffusion sensitivity factor b having the high diffusion sensitivity value, and an apparent diffusion coefficient map calculated by the Diffusion-weighted image and the T2-weighted image. The Diffusion-weighted image is referred to as DWI. The apparent diffusion coefficient map is referred to as ADC map.

In step S2, a brain tissue and a non-brain tissue are calculated in accordance with the T2-weighted image, and a brain image (x, y, z) is obtained and used to locate the ADC map to obtain relevant parameters. The brain image (x, y, z) has removed the non-brain tissue.

In Step S3, the ADC map corresponding to the brain image (x, y, z) is binarized via a ADC threshold thADC2 of the transition area. Therefore, a binary image B_ADC (x, y, z) is obtained.

In step S4, the core area and the transition area are estimated via a binary image and a ADC threshold thADC1 of the core area.

In step S5, the core area and the transition area are obtained via processing DWI high signal characteristic parameters of the core area in accordance with high signal constraint processing.

In step S6, characteristic parameters of the core area and the transition area are calculated. The characteristic parameters of the core area and the transition area include: volume of the core volCore, volume of the transition volIP, an ADC gradient of the transition area gradAvgN, a radial distance of the transition area δR, a total change of ADC gradient of the transition area δADC, a mean ADC value of the core area AvgADC, a mean square errors of ADC value of the core area SdADC, a variation coefficient of ADC value of the core area CV, a change of the mean ADC value of partial edge area of the core area adjacent to the transition area δAvgADC, a change of the mean square errors of ADC value of partial edge area of the core area adjacent to the transition area δSdADC, and a variation coefficient of ADC value of partial edge area of the core area adjacent to the transition area δCvADC.

S1 Step Process:

The present disclosure is implemented in accordance with the magnetic resonance DWI of patient with acute cerebral ischemia. An image mainly related to the DWI includes:

(1) A diffusion sensitivity factor b=0 in the T2-weighted images.

(2) An isotropic DWI having the high diffusion sensitivity value b of common clinical is 1000 s/mm$^2$, or 1500 s/mm$^2$.

(3) An ADC map calculated by the DWI and the T2-weighted image.

Coordinates of the T2-weighted images, the isotropic DWI, and the ADC map are set to: X-axis extending from left to right, Y-axis extending from front to back, Z-axis extending from top to bottom. A slice whose Z coordinate is a constant is referred to an axial slice. A slice whose Y coordinate is a constant is referred to a coronal slice. A slice whose X coordinate is a constant referred to a sagittal section slice. The Z coordinate of the nth axial slices is n, wherein the n is a natural number. In the following description of the present disclosure, for example, the axial slices is obtained by an axial clinical images of patient. It is to be understood that the coronal slice and the sagittal section slice can also be obtained by the same way.

A coordinate system, the number of voxels and physical locations of patient corresponding to the same voxel of the T2-weighted images, the DWI and the ADC map are same. A T2 (x, y, z), a DWI(x, y, z), and a ADC (x, y, z) represent gray scales of one voxel (x, y, z) in the T2-weighted image, the DWI and the ADC map, respectively. The ADC(x, y, z) is calculated by the follow formulas:

$$ADC(x,y,z)=\log(T2(x,y,z)/DWI(x,y,z))/b;$$

Wherein log represents natural logarithm, b is a constant with a range from about 1000 to 1500 high diffusion coefficient gradient used in DWI. In order to reduce noise impacts, processing the T2 (x, y, z) and/or the DWI(x, y, z) in accordance with median filter before calculating ADC value.

Figure 2:
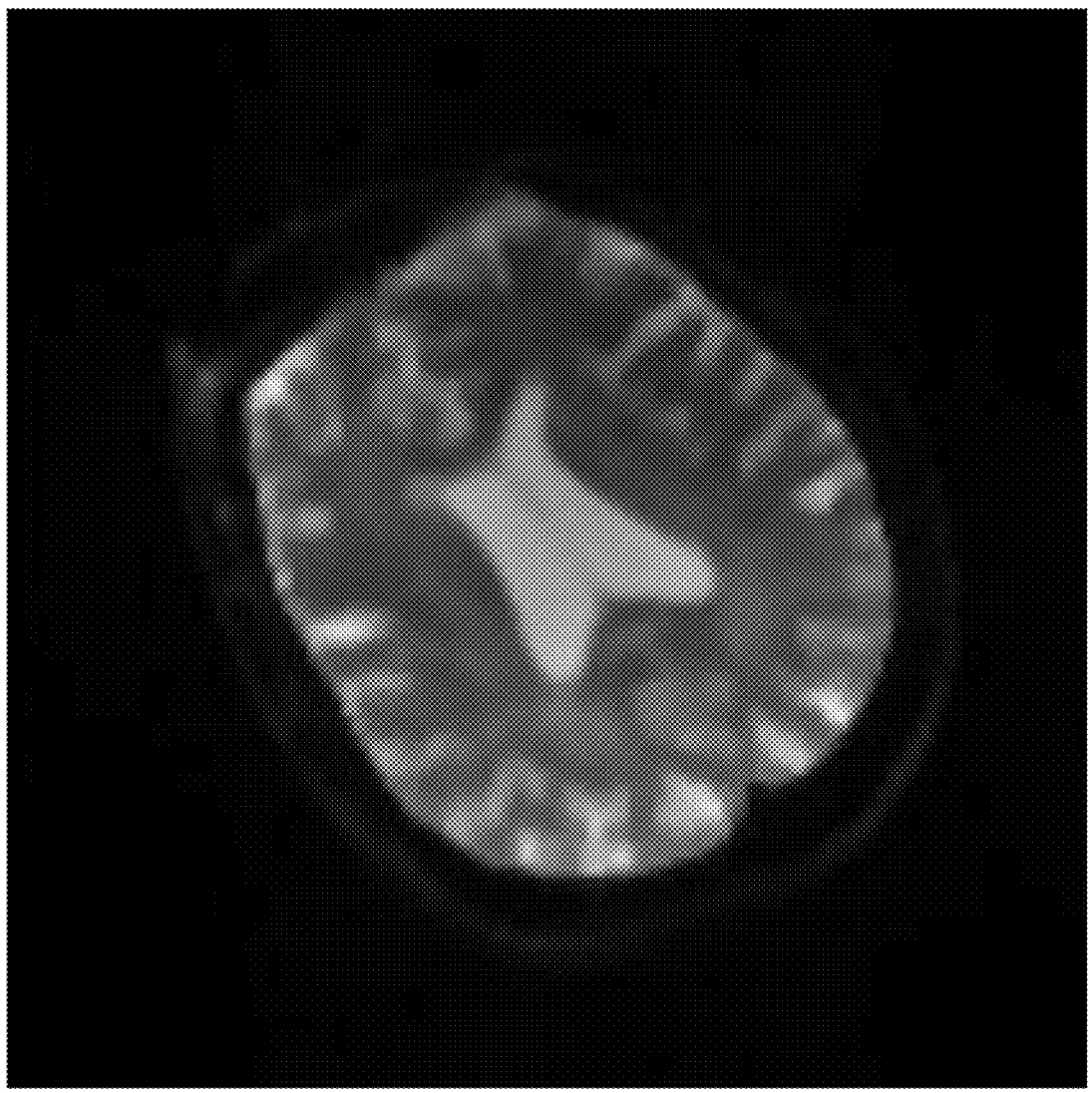
FIG. 2 is an image of original slices of a T2-weighted image.

As previously mentioned, the DWI, the T2-weighted image and the ADC map of patient with the initial acute phase of cerebral infarction have the same coordinate system. The same coordinate system represents the same physical location of patient, and storage for a standard DICOM format. The DWI(x, y, z), the T2 (x, y, z) and the ADC (x, y, z) are 16-bit data, and the T2-weighted image is shown in FIG. 2. Space coordinates of each voxel (x, y, z) have the following constraints, that is, 0≤x≤xSize−1, 0≤y≤ySize−1, 0≤z≤zSize−1; wherein x, y, z are non-negative integer; xSize, ySize, and zSize represent the number of voxels of three-dimensional image in the x, y, and z direction, starting from the number 0. In the X, Y and Z direction, the physical size of each voxel is referred to voxX, voxY, and voxZ in mm/voxel.

Because gray scale of voxels of an actual three-dimensional image is only effective in the hundreds or thousands, 16-bit data of the T2-weighted image is converted to 8-bit data in order to improve image-processing speed. The 16-bit data can be converted to the 8-bit data by a variety of implementations. In one embodiment, the 16-bit data is converted to 8-bit data via excluding isolated voxels from the T2-weighted image, which can be referred to as the percentile-based method. The isolated voxels are the maximum gray scale level and the lowest gray scale level of voxels. The percentile-based method includes the following steps.

Firstly, a percentage of low gray $P_0$ and a percentage of high gray $P_1$ are set. In one embodiment, the percentage of low gray $P_0$ is 0.01%, the percentage of high gray $P_1$ is also 0.01%.

Then, a gray scale value $g_0$ and a gray scale value $g_1$ respectively corresponding to the percentage of low gray scale $P_0$ and the percentage of high gray scale $P_1$ are calculated. A percentage of the number of voxels of which gray scale between 0 to $g_0$ in all voxels is less than $P_0$. A percentage of the number of voxels of which gray scale between 0 to $g_0+1$ in all voxels is greater than $P_0$. A percentage of the number of which voxels of which gray scale greater than $g_1$ in all voxels is less than $P_1$. A percentage of the number of voxels of which gray scale greater than g1−1 in all voxels is greater than $P_1$. According to the gray scale value $g_0$ and the gray scale value $g_1$, the original T2 (x, y, z) is coverted to a T2_8 (x, y, z) by the following formula (1). The T2_8 (x, y, z) represent a 8-bit T2-weighted image, and is calculated by formula (1).

$$T2\_8(x, y, z) = \begin{cases} 0 & T2(x, y, z) < g_0 \\ 255 \times (T2(x, y, z))/(g_1 - g_0) & g_0 \le T2(x, y, z) \le g_1 \\ 255 & T2(x, y, z) > g_0 \end{cases} \quad (1)$$

In addition, the DWI and the ADC map can also be obtained by a 8-bit ADC map DWI_8(x, y, z) and ADC_8 (x, y, z), or obtained completely similar to the above steps.

It should be pointed that process of the data from step S1 to step S4 is in accordance with the 8-bit DWI_8(x, y, z), the 8-bit T2_8 (x, y, z) and the 8-bit ADC_8 (x, y, z). In fact, the above formula (1) is used to calculate the 8-bit T2-weighted image. If the number "255" of the formula (1) is replaced with "15", the T2_8 (x, y, z) represent a 4-bit T2-weighted image.

S2 Step Process:

Referring to FIG. 1, in one embodiment, an image brain (x, y, z) of the brain tissue is removed the non-brain tissue in accordance with a gray scale threshold Th1 and an automatic segmentation process of the mathematic morphology. The image brain (x, y, z) of the brain tissue is mainly includes images of cerebro-spinal fluid (CSF), gray scale matter and white matter.

Firstly, the gray scale threshold Th1 is obtained by dividing the 8-bit T2-weighted image T2_8 (x, y, z) into I-IV class whose gray scale from low to high. In one embodiment, the 8-bit T2-weighted image T2_8 (x, y, z) is divided into I-IV class by the fuzzy C-means clustering (Fuzzy C-means Clustering, referred to as FCM). The gray scale threshold Th1 is the maximum value of I class, which excluding low signal threshold value Th1 of image of the non-brain tissue.

Secondly, the T2_8 (x, y, z) is binarized to obtain a binary image B1 (x, y, z). In one embodiment, if gray scale of one pixel of the T2_8 (x, y, z) is not less than the gray scale threshold Th1, set to 1, which is the foreground; otherwise, set to 0, which is the background.

Thirdly, the largest connected area of the binary image B1 (x, y, z) is found. Each pixel of the argest connected area is correspond to a pixel of the binary image B1 (x, y, z), and connected to each other in space.

Figure 3:
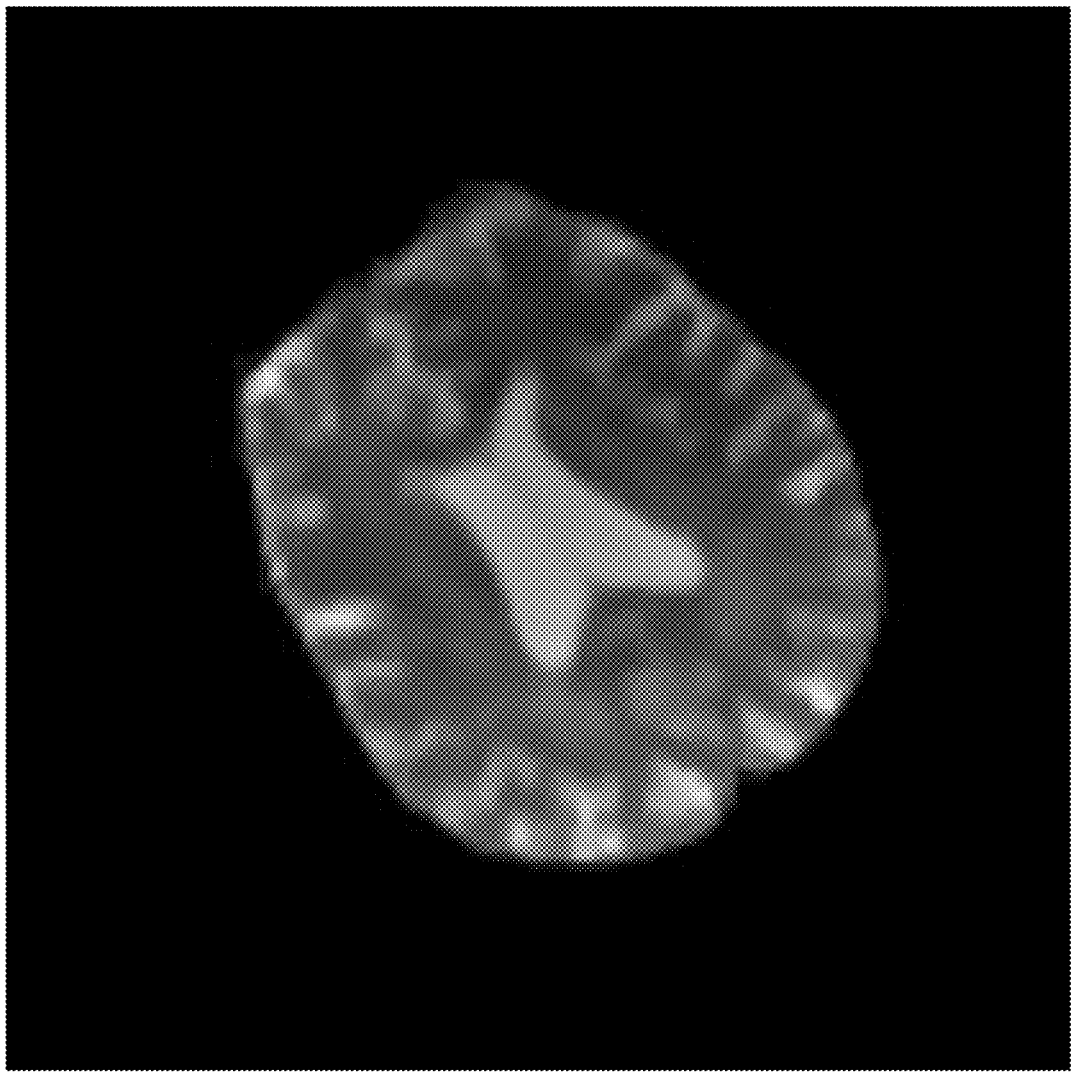
FIG. 3 is a brain image calculated in accordance with FIG. 2.

Finally, axial slices of the largest connected area are opened in the mathematical morphology. In one embodiment, axial slices of the largest connected area are opened via using a structuring element, such that connection between the brain tissue and the non-brain tissue is cut off, then the brain tissue will be reserved for 1. The structuring element is a square of side length of 10 mm. The opened largest connected area is found to fill in the each axial slice. Therefore, apertures of the brain tissue are set to a foreground voxel, resulting in that the brain image (x, y, z) is obtained, shown in FIG. 3. The brain image (x, y, z) becomes smooth, break off the narrow and eliminate thin protrusions because of the opened axial slices of the largest connected area.

Figure 4:
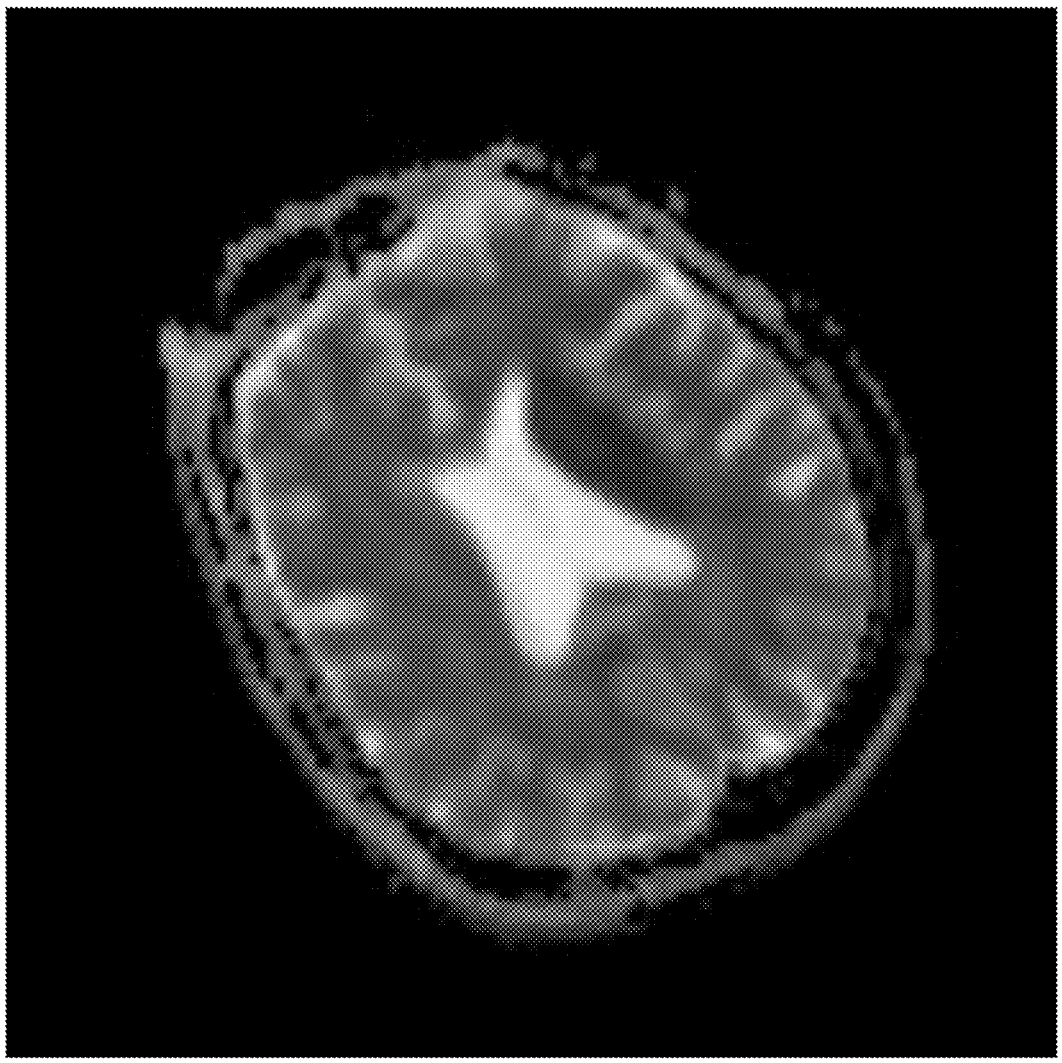
FIG. 4 is an ADC map having a coordinates system which is same to that of the original slices shown in FIG. 2.

S3 Step Process:

The non-brain tissue of the T2 weighted image is removed in step S2. The DWI, the T2-weighted image and the ADC map have the same coordinates system and the same corresponding voxels. When the ADC map shown in FIG. 4 is binarized, voxels of the brain tissue are only binarized, which is called low signal constraint binarizing. The binary process of voxels of the brain tissue see as follow.

When ADC value of a pixel is greater than a ADC threshold thADC$_2$ of the transition area, the pixel is a background pixel. When the ADC value of a pixel is less than or equal to the ADC threshold thADC$_2$ of the transition area, the pixel is a foreground pixel. The ADC_8 (x, y, z) is converted to a binary image B_ADC (x, y, z) according to the following formula (2).

$$B\_ADC(x, y, z) = \begin{cases} 1 & ADC\_8(x, y, z) \leq thADC_2 \\ 0 & ADC\_8(x, y, z) > thADC_2 \end{cases} \quad (2)$$

The ADC threshold thADC$_2$ of the transition area can be calculated by the following formula (3):

$$thADC_2 = P_2 \times ADC_{ref} \quad (3)$$

wherein the P$_2$ is a constant between 0 and 1. In one embodiment, the P2 is a constant between 0.75 and 0.90.

In addition, a ADC threshold thADC$_1$ of the core area can be calculated by the following formula (4):

$$thADC_1 = P_1 \times ADC_{ref} \quad (4)$$

wherein the P$_1$ is a constant between 0 and 1. In one embodiment, the P$_1$ is a constant between 0.55 and 0.70.

The P$_1$ and the P$_2$ are set by experiments. The ADC$_{ref}$ of the formulas (3) and (4) is an ADC value of the normal brain tissue. The brain image brain (x, y, z) determined in step S2 mainly includes images of the cerebrospinal fluid, the gray matter and the white matter. The ADC value of the cerebrospinal fluid is higher, but ADC value of the normal gray matter is similar to that of the white matter. The ADC$_{ref}$ is determined by the following steps: firstly, occurrence times of all ADC values of brain tissue of the ADC_8 (x, y, z) are counted; and then, the ADC values of the normal brain tissue are determined based to the counted occurrence times, which is denoted by the ADC$_{ref}$. The ADC values of the normal brain tissue can be any value in neighborhood scope of the most frequent of ADC values. For example, the ADC values of the normal brain tissue can be referred to ADC$_{ref}$=ADC$_{max}$±5, wherein the ADC$_{max}$ represents ADC value of the highest occurrence times. In a preferred embodiment, ADC$_{ref}$=ADC$_{max}$. It should be pointed that, images of the brain tissue and the non-brain tissue are only distinguished between the brain and the non brain, not distinguished between different brain tissues, such as the gray matter and the white matter, the hippocampus.

In an embodiment, the brain image usually includes images of at least one brain slice. When the ADC threshold of the core area and the transition area are calculated, the ADC value of the normal brain tissue is comprehensive assessment of each slice image data. The ADC value of the normal brain tissue is used to calculate the ADC thresholds of the core area and the transition area, then, each axial slice is calculated by one ADC threshold in the binarization process. In an alternative embodiment, the ADC value of each axial slice is calculated, and the highest occurrence times of the ADC value is selected from all the ADC values. The ADC value of the normal brain tissue is a nearby value of the highest frequency of occurrence of the ADC value. In other words, the ADC value of the normal brain tissue is any value selected from the neighborhood scope of the highest frequency of occurrence of the ADC value. Therefore, the ADC thresholds of the core area and the transition area are calculated by the formulas (3) and (4); the binary image B_ADC (x, y, z) of each axial slice is calculated by formula (2).

S4 Step Process:

Estimation process of the core area and the transition area includes the following steps:

Firstly, the foreground connected area of each slice is obtained in accordance with the binary image B_ADC (x, y, z).

Secondly, the foreground connected area is divided into a foreground area and a background area. The foreground area is a part of the foreground connected area whose volume is not less than a first preset volume num$_0$, and includes a plurality of voxels of volume which is not less than a second preset volume num$_1$, the ADC value of which is smaller than the threshold thADC$_1$ of the core area. In one embodiment, the first preset volume num$_0$ is 150 mm$^3$; the second preset volume num$_1$ is 15 mm$^3$. The background area is other part of the foreground connected area excluding the foreground area. In other words, the first image B1_ADC (x, y, z) is obtained via excluding the foreground area. It should be pointed that, the connected area and the brain boundary are different, and distance from the brain boundary to the connected area is calculated to prevent from partial volume effecting. In a preferred embodiment, the maximum distance from the brain boundary to the connected area is not less than 10 mm.

In the above process, the first preset volume num$_0$ and the first preset volume num$_0$ is set in order to remove small artifacts of the ADC map. Volume size limitation of the first preset volume num$_0$ and the second preset volume num$_1$ can reduce impact of noise. The first preset volume num$_0$ limits total volume of the core area and the transition area. The second preset volume num$_1$ limits the number of voxels of the core area or volume of the core area. Relations of the first preset volume num$_0$ and the total volume of the core area and the transition area, and relations of the second preset volume num$_1$ and the number of voxels of the core area or volume of the core area are determined by experiment.

Figure 5:
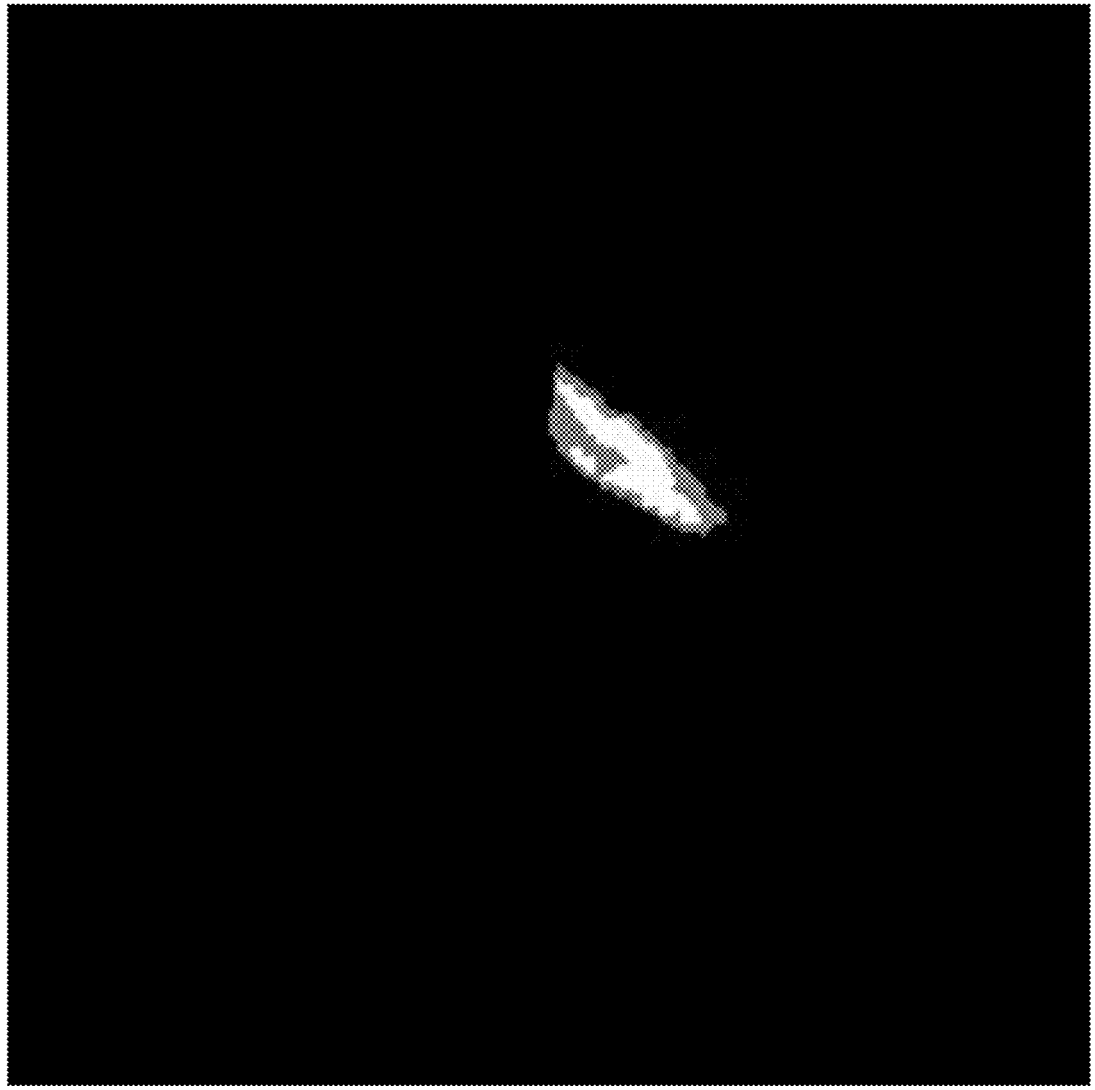
FIG. 5 is an ADC map having a core area (in white color) and a transition area (in gray color) corresponding to the ADC map shown in FIG. 4.

FIG. 4 is an original unprocessed ADC map. FIG. 5 is a processed ADC map. Referring to FIG. 5, the estimated transition area A and the estimated transition area B are calculated, which are correspond to the ADC map shown in FIG. 2.

S5 Step Process:

Because of acute phase of cerebral ischemia should correspond to the DWI high signal and ADC low signal, S5 step further includes high signal constraint of DWI in order to prevent misjudgment based on low ADC value.

High signal constraint of DWI is reflected in the core area. Generally, if the core area in an axial slice z, denote the mean gray scale of DWI of the core area to DWIAvgF, denote the DWI gray scale of all voxels adjacent to the core area to DWIAvgB. For the axial slice z, denote all voxels of the brain tissue of which DWI(x, y, z) is no less than a constant to (x, y z), denote mean gray scale and standard deviation of (x, y, z) in DWI to AvgDWI(z) and SdDWI(z). The constant is corresponding to voxels of non-CSF, and the constant can be 40. Denote threshold of high signal to DWITh(z), and DWITh(z) is calculated by the following formula: DWITh(z)= AvgDWI(z)+CC1*SdDWI(z), wherein CC1 represents a constant, CC1 is a range from about 1.1 to about 1.5, * represents multiplication. For the core area and the transition area in the axial slice z, if (DWIAvgF−DWIAvgB)>CC2 or (DWIAvgF−DWITh(z))>CC3, the core area and the transition area of the first image B1_ADC(x, y, z) are retained; if not, the core area and the transition area is background; wherein CC2 and CC3 represents constants, CC2 is a range from about 10 to about 20, and CC3 is a range from about 4 to about 8.

Figure 6:
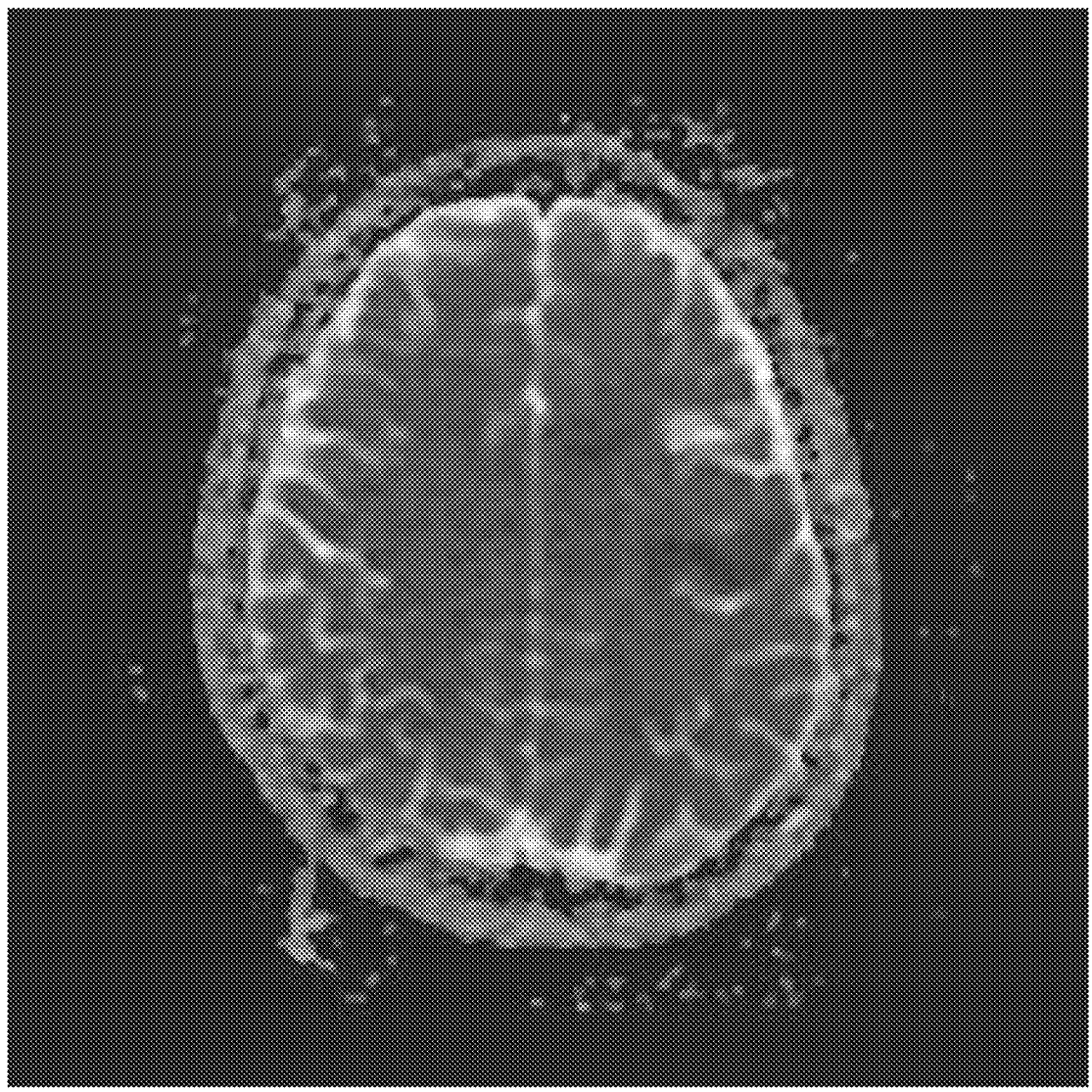
FIG. 6 to FIG. 9 are comparison charts for non-using of high signal processing DWIs and using of high signal processing DWI.
Figure 7:
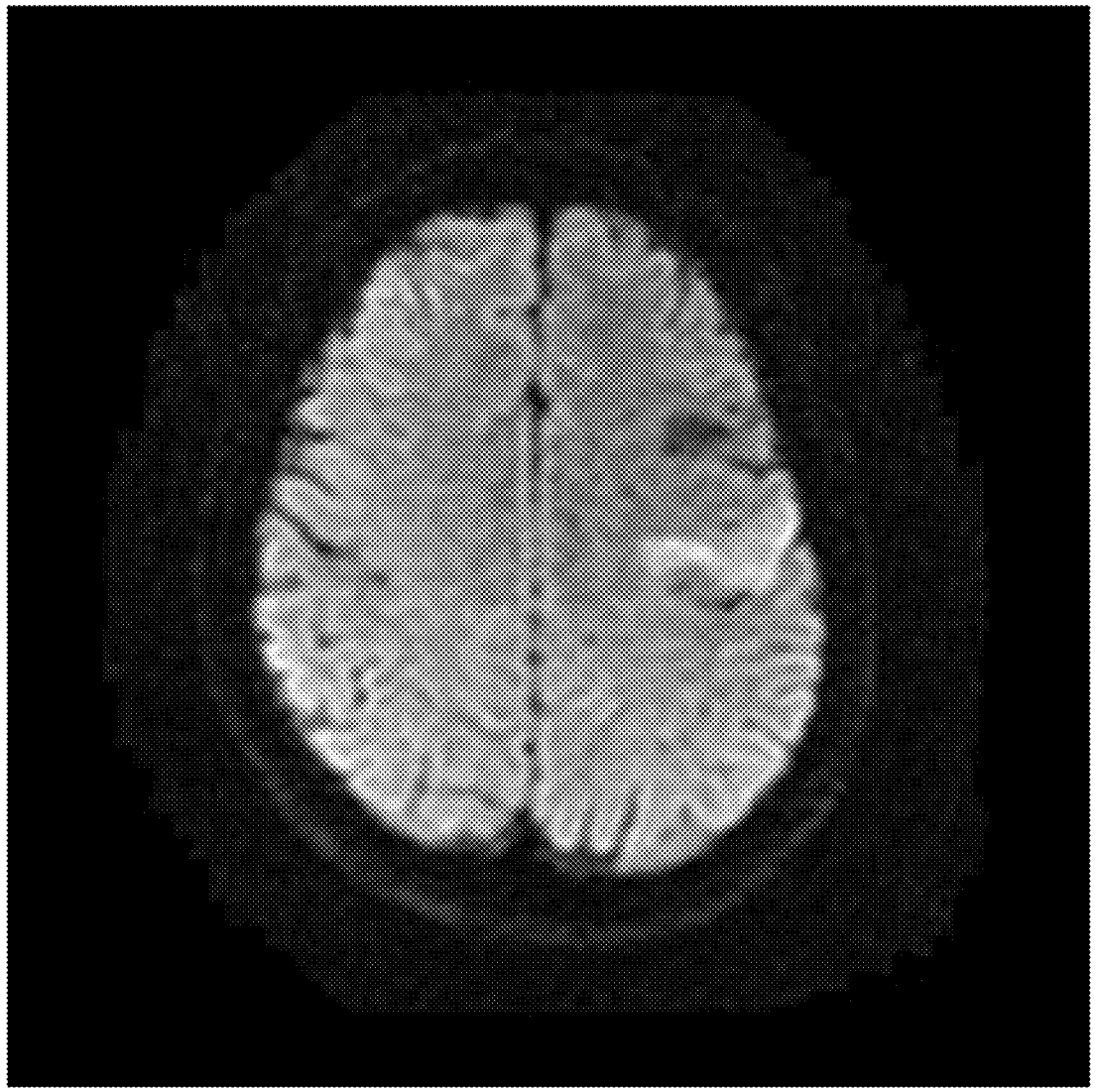
Figure 8:
Figure 9:

FIG. 6 and FIG. 7 are ADC map and DWI scanned with the same slice of the same patient in the same time. There are two low signal areas in the ADC map, and there is only one high signal area in the DWI. Estimated low signal core area (in white color) and the transition region (in gray color) based on ADC are showed in FIG. 8, there are two "core area and transition area" corresponding to the two low signal areas in ADC map, wherein the top one of the low signal area should be artifact as it does not show a high signal in DWI. Detected "core area and transition area" based on method of "high signal of DWI and low signal of ADC map" is showed in FIG. 9, there is only one area with high signal in DWI and with low signal in ADC map, and areas with low signal in ADC map and without high signal in DWI have been excluded.

In addition to the above steps, S5 step further includes a recovering process according to turning background voxels nearby to foreground voxels. The recovering process includes the following steps: finding the adjacent voxels of each foreground voxel of the first image B1_ADC (x, y, z); setting the voxel of which ADC value not greater than the threshold $thADC_2$ of the transition area as the foreground voxel. For example, when a foreground voxel $(x_0, y_0, z)$ of the B1_ADC (x, y, z) is processed, the adjacent voxels $(x_0-1, y_0, z_0-1)$, $(x_0, y_0-1, z_0-1)$, $(x_0+1, y_0-1, z_0-1)$, $(x_0-1, y_0, z_0-1)$, $(x_0, y_0, z_0-1)$, $(x_0+1, y_0, z_0-1)$, $(x_0-1, y_0+1, z_0-1)$, $(x_0, y_0+1, z_0-1)$, $(x_0+1, y_0+1, z_0-1)$, $(x_0-1, y_0, z_0+1)$, $(x_0, y_0-1, z_0+1)$, $(x_0+1, y_0-1, z_0+1)$, $(x_0-1, y_0, z_0+1)$, $(x_0, y_0, z_0+1)$, $(x_0+1, y_0, z_0+1)$, $(x_0-1, y_0+1, z_0+1)$, $(x_0, y_0+1, z_0+1)$, $(x_0+1, y_0+1, z_0-1)$ are found. If the ADC value of the adjacent voxel is less than the ADC threshold $thADC_2$, the adjacent voxels are setted as the foreground voxels.

Furthermore, S5 step further includes a process of a second removing artifacts. The process of the third removing artifacts includes: finding the foreground connected area of each slice of the first image B1_ADC (x, y, z); setting a partial area of the foreground connected area as the background area, volume of the background area is smaller than the third preset volume $num_2$ (such as 15 mm$^3$)

In order to optimize image quality, the above images can be performed of above processing, and then performed the following steps.

Finally, an estimated core area and an estimated transition area are defined. The estimated core area is a set of voxels of the first image B1_ADC (x, y, z) of which ADC value less than the ADC threshold $thADC_1$ of the core area. The estimated transition area is a set of voxels of the first image B1_ADC (x, y, z) of which ADC value between the ADC threshold $thADC_1$ of the core area and the threshold $thADC_2$ of the transition area. The numCore represents the number of voxels of the estimated core area. The numIP represents the number of voxels of the estimated transition area. Volume volCore of the estimated core area and volume volIP of the estimated transition area are calculated by the formula (5). The volume volCore of the estimated core area represents volume of core areas of all slices. The volume volIP of the estimated transition area represents volume of transition areas of all slices.

$$volCore = voxX \times voxY \times voxZ \times numCore;$$

$$volIP = voxX \times voxY \times voxZ \times numIP \qquad (5)$$

S6 Step Process:

Step S6 is used to calculate characteristic parameters of the core area and the transition area. The characteristic parameters of the estimated area are calculated via selecting at least one connected area from the estimated transition area. The at least one connected area has the largest voxels, and can be located at different slices. The at least one connected area is selected in order to eliminate impacts of the smaller connected area. If at least two connected areas are selected, the characteristic parameters of the at least two connected areas are calculated respectively. The maximum or minimum value of the characteristic parameters are obtained by comparing with the characteristic parameters of the at least two connected areas.

For example, a connected area that has the most voxels of the core area and the transition area and a connected area that has the most voxels of the core area are selected. The characteristic parameters of the two selected connected areas are calculated as the following method.

(1) ADC Gradient gradAvgN of the Transition Area

Firstly, the two connected areas which have the largest foreground voxels are found in axial slices of the first image B1_ADC (x, y, z) of step S4 or step S5. $Cmt_1$ (x, y, z) and $Cmt_2$ (x, y, z) represent a set of two-dimensional points of the two connected areas.

Secondly, set of interior point of the two connected areas is found. The set of interior points of two-dimensional point are the two-dimensional points, which of itself and eight neighboring points belong to this set. In other words, all $(x_0, y_0)$ are interior points of set A (x, y), wherein $(x_0, y_0) \in A$, and $(x_0-1, y_0) \in A$, $(x_0+1, y_0) \in A$, $(x_0-1, y_0-1) \in A$, $(x_0, y_0-1) \in A$, $(x_0+1, y_0-1) \in A$, $(x_0-1, y_0+1) \in A$, $(x_0, y_0+1) \in A$, $(x_0+1, y_0+1) \in A$.

Thirdly, the ADC gradient of each interior point $(x_0, y_0, z_0)$ of the $Cmt_1$ (x, y, z) and the $Cmt_2$ (x, y, z) is calculated. In an embodiment, when the ADC value of the interior point $(x_0, y_0, z_0)$ between the ADC threshold thADC1 and the ADC threshold thADC2, gradient of the interior point $(x_0, y_0, z_0)$ is equal to a difference between the maximum ADC value of the four adjacent voxels $(x_0-1, y_0, z_0)$, $(x_0+1, y_0, z_0)$, $(x_0, y_0-1, z_0)$, $(x_0, y_0+1, z_0)$ and the ADC value of the interior point $(x_0, y_0, z_0)$. In an alternative embodiment, the gradient of ADC of the interior point $(x_0, y_0, z_0)$ can also be equal to a difference between the maximum ADC value of four diagonal positions $(x_0-1, y_0-1, z_0)$, $(x_0+1, y_0-1, z_0)$, $(x_0-1, y_0+1, z_0)$, $(x_0+1,$ $y_0+1, z_0$) and the ADC value of the interior point ($x_0, y_0, z_0$) divided by 1.414. A larger gradient of ADC is selected from the two gradients of ADC shown in the above embodiments, and the minimum value of the larger gradient is limited to 0. That is to say, gradient of ADC of each interior point is obtained by the following step: obtaining difference between the ADC value of the adjacent voxels and the ADC value of the interior point; dividing the difference between the ADC value of the adjacent voxels and the ADC value of the interior point by a distance between the adjacent voxels and the interior point. The gradients of ADC of the interior points of the $Cmt_1$ (x, y, z), $Cmt_2$ (x, y, z) that between the threshold of ADC thADC1, thADC2 are averaged, which are recorded as gradAvg1 and gradAvg2.

Fourthly, the ADC values of the $Cmt_1$ (x, y, z) and the $Cmt_2$ (x, y, z) between the threshold thADC1 and the threshold thADC2 are averaged, which are recorded as avgADC1 and avgADC2.

Finally, according to the following formulas (6) and (7), regularized gradients and gradAvgN$_2$ are calculated by regularization process, respectively.

$$gradAvgN_1 = gradAvg1 \times 0.73/(ADC_{ref} \times avgADC1) \quad (6)$$

$$gradAvgN_2 = gradAvg2 \times 0.73/(ADC_{ref} \times avgADC2) \quad (7)$$

The regularization process can eliminate the impact of the averaged ADC value, which should be inversely proportional to the averaged ADC value. In accordance with experience, the averaged ADC is usually equal to 0.73. It should be pointed that 0.73 can be replaced by any positive number.

In order to balance the impact of changes, an output of the gradient of ADC of the transition area is the maximum value of the gradAvgN$_1$ and the gradAvgN$_2$, which is calculated by the following formula:

$$gradAvgN = max(gradAvgN_1, gradAvgN_2).$$

(2) radial distance $\delta R$ of the transition area

The number of voxels of the $Cmt_1$ (x, y, z) of which ADC value less than the ADC threshold thADC1 is $N_{10}$. The number of voxels of the Cmt1 (x, y, z) of which ADC value between the ADC threshold thADC1 and the threshold ADC thADC2 is $N_{11}$. The number of voxels of the $Cmt_2$ (x, y, z) of which ADC value being less than the ADC threshold ADC1 is $N_{20}$. The number of voxels of the $Cmt_2$ (x, y, z) of which ADC value between the threshold thADC1 and the ADC threshold ADC2 is $N_{21}$. The $N_{10}$, $N_{11}$, $N_{20}$, $N_{21}$ are calculated by the following formula (8), (9), (10), (11) respectively.

$$R_{10} = sqrt(N_{10}/3.1416) \quad (8)$$

$$R_{11} = sqrt((N_{10}+N_{11})/3.1416) \quad (9)$$

$$R_{20} = sqrt(N_{20}/3.1416) \quad (10)$$

$$R_{21} = sqrt((N_{20}+N_{21})/3.1416) \quad (11)$$

The core area and the transition area are approximate to a round. $R_{10}$ is a radius of the core area of the first connected area $Cmt_1$ (x, y, z). $R_{11}$ is a radius of the core area and the transition area of the first connected area $Cmt_1$ (x, y, z). $R_{20}$ is a radius of the core area of the second connected area $Cmt_2$ (x, y, z). $R_{21}$ is a radius of the core area and the transition area of the second connected area $Cmt_2$ (x, y, z). Therefore, ($R_{11}-R_{10}$) and ($R_{21}-R_{20}$) represents radial distances of the estimated transition area.

In order to balance the impact of changes, output of the radial distance $\delta R$ of the transition area is the maximum value of ($R_{11}-R_{10}$) and ($R_{21}-R_{20}$), which is calculated by the following formula:

$$\delta R = max(R_{11}-R_{10}, R_{21}-R_{20}).$$

(3) total change of radial ADC $\delta ADC$ of the transition area

Total change of radial ADC $\delta ADC1$, $\delta ADC2$ of the estimated transition area of the first and second connected area are calculated by the radial distance and the mean gradient of the estimated transition area, which are calculated by the following formulas:

$$\delta ADC1 = gradAvgN_1 \times (R_{11}-R_{10})/ADC_{ref};$$

$$\delta ADC2 = gradAvgN_2 \times (R_{21}-R_{20})/ADC_{ref}.$$

In order to balance the impact of changes, output of total $\delta ADC$ of the transition area is the minimum value of the $\delta ADC1$ and the $\delta ADC2$:

$$\delta ADC = min(\delta ADC1, \delta ADC2).$$

(4) variation coefficient of established cerebral infarction area of the two connected areas $Cmt_1$ (x, y, z) and $Cmt_2$ (x, y, z) is determined as follows: when the voxel ($x_0, y_0, z_0$)$\in Cmt_1$ (x, y, z) or $Cmt_2$ (x, y, z), and the ADC value of the voxel ($x_0, y_0, z_0$) is less than the ADC threshold thADC1, mean ADC values and mean square errors of the voxel ($x_0, y_0, z_0$) are calculated, which are avgADC1, avgADC2 and sdADC$_1$, sdADC$_2$. Variation coefficient of ADC of the first connected area $Cmt_1$ (x, y, z) is $CV_1$. Variation coefficient of ADC of the second connected area $Cmt_2$ (x, y, z) is $CV_2$.

$$CV_1 = sdADC_1/avgADC_1;$$

$$CV_2 = sdADC_2/avgADC_2.$$

The volume ratio volRatio is, volRatio=volIP/volCore, wherein the volIP and the volCore are a volume of the transition area and the core area.

(5) parameters of partial edge area of the core area adjacent to the transition area A mean ADC value and a mean square errors of voxels of all core area are calculated, the mean ADC value and the mean square errors represent to AvgADC$_{core}$ and SdACD$_{core}$. Eroding the core area by 3×3 mathematical morphology erosion, and a mean ADC value and a mean square errors of the remaining core area represent to AvgADC$_{coreE}$ and SdACD$_{coreE}$.

The change of the mean ADC of partial edge area of the core area adjacent to the transition area is calculated by the following formulas:

$$\delta AvgADC = (AvgADC_{core} - AvgADC_{coreE})/AvgADC_{core}.$$

The change of the mean square errors of ADC of partial edge area of the core area adjacent to the transition area is calculated by the following formulas:

$$\delta SdADC = (SdADC_{core} - SdADC_{coreE})/SdADC_{core}.$$

The change of the variation coefficient of ADC of partial edge area of the core area adjacent to the transition area is calculated by the following formulas:

$$\delta CvADC = \delta SdADC/\delta AvgADC.$$

According to the above parameters, whether there is "ischemic brain tissue can be saved" and whether thrombolysis can be implemented are analyzed. In medicine, the "ischemic brain tissue can be saved" is determined by positron emission tomography (PET), and is approached by "unmatch" in clinical. The "unmatch" is determined by an abnormal volume of the PWI and the DWI. If the abnormal volume is greater than 1.2 times of volume of the DWI, there is "unmatch" which implies the existence of "ischemic brain tissue can be saved"; if not, there is no "unmatch". In accordance with the above method, a set of training data needs to be established through the application and analysis in clinical or experiment, which is used to determine the three characteristic parameters threshold $\theta_{ADC}$, $\theta_r$, $\theta_{vol}$, corresponding to $\delta ADC$, volRatio, volCore. For example, $\theta_{ADC}=0.180$, $\theta_{vol}=100$ ml, that is, when $\delta ADC<0.180$ or volCore>100 ml, there is no "ischemic brain tissue can be saved"; otherwise, there is "ischemic brain tissue can be saved". Whether there is "ischemic brain tissue can be saved" should be determined by $\delta ADC$ or volCore.

For indications of the thrombolysis, a set of training data needs to be established through the application and analysis in clinical or experiment. The set of training data includes datas of inexecution thrombolysis and execution thrombolysis. The data of inexecution thrombolysis includes data of patient completely disappeared and data of patient improved symptoms by the thrombolysis. The data of execution thrombolysis includes data of patient completely disappeared, data of patient improved symptoms without the thrombolysis, and data of patient become worse after thrombolytic therapy.

Parameters of the set of training data include the above parameters $CV_1$ and $CV_2$, $\delta ADC1$ and $\delta ADC2$, volRatio, volCore, $\delta AvgADC$, $\delta SdADC$, and $\delta CvADC$. For example, a possible indication of thrombolysis means: if $\delta CvADC$ is less than 2 and there is "ischemic brain tissue can be saved", output of determination conclusion is recommending thrombolysis; if not, output of the determination conclusion is not recommending thrombolysis. A general indication of thrombolysis means: the indication of thrombolysis is determined in accordance with the gradient of ADC the transition area, the radial distance of the transition area, the total change of ADC of the transition area, the mean ADC value of the core area, the variation coefficient of ADC of the core area, volume and the volume ratio of the core area and the transition area, the change of a mean ADC of partial edge area of the core area adjacent to the, the change of the mean square errors of ADC of partial edge area of the core area adjacent to the transition area, and the change of the variation coefficient of ADC of partial edge area of the core area adjacent to the transition area of training. In other words, the general indication of thrombolysis depends on the limitation or range of the parameters mentioned before, the limitation or range can be obtained by training, and is used for some indications rules.

Embodiment 2

Figure 10:
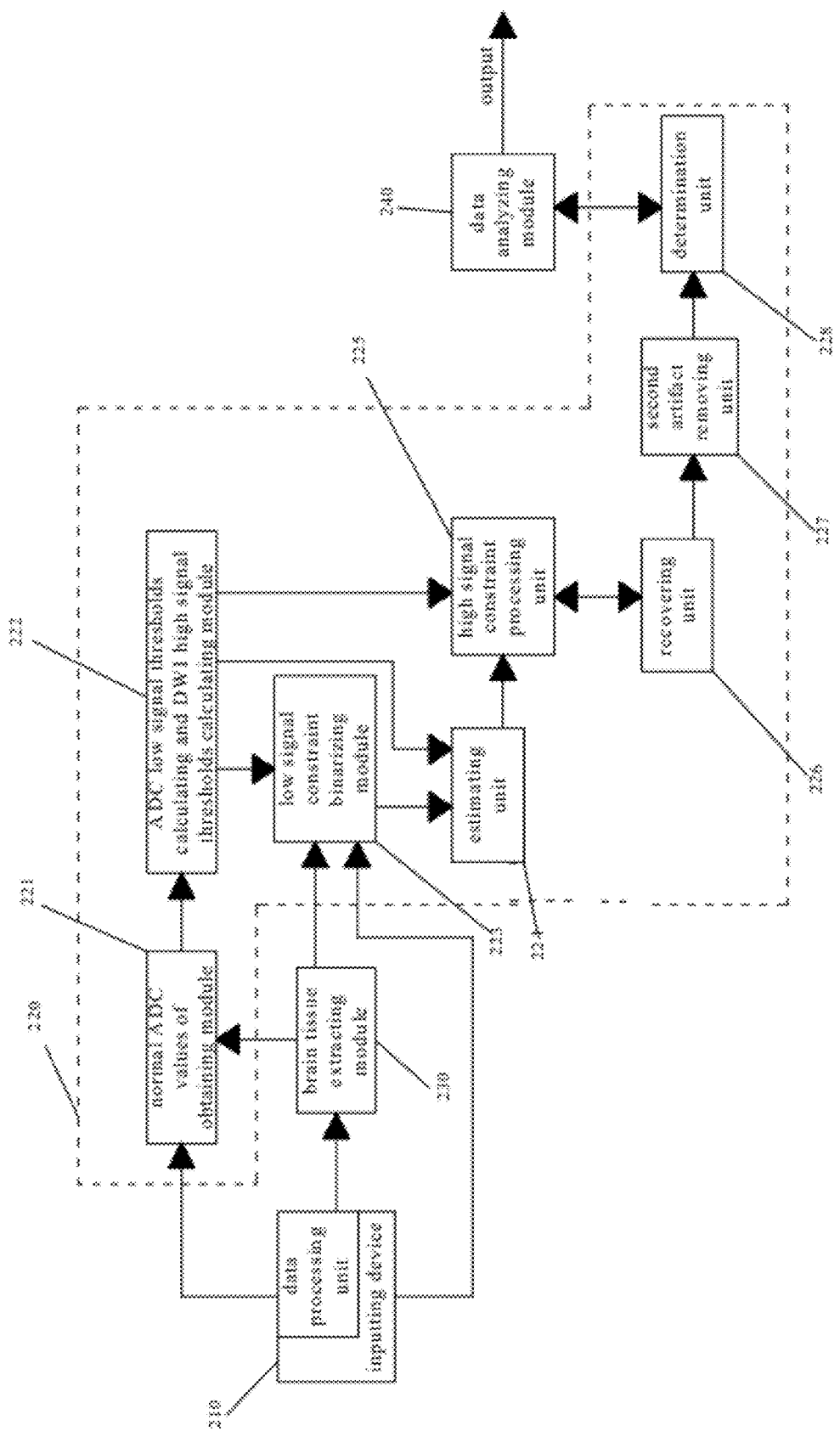
FIG. 10 is a block diagram of one embodiment of system for obtaining brain characteristic parameters including an estimating unit.

System for obtaining brain characteristic parameters:

Referring to FIG. 10, a system of obtaining brain characteristic parameters includes: an inputting device 210, an image processing module 220, a brain tissue extracting module 230, and a characteristic parameters calculating unit 240. The inputting device 210 is used to obtain a magnetic resonance perfusion weighted imaging of a patient obtained in accordance with magnetic resonance, wherein the magnetic resonance perfusion weighted imaging includes a DWI, T2-weighted image, and an ADC map. The brain tissue extracting module 230 is used to calculate a brain tissue of patient in accordance with the T2-weighted image, and output a brain image. The image processing module 220 is used to obtain a binary image based on binarizing the voxels of the ADC map corresponding to the brain tissue image in accordance with ADC low signal constraint binarizing according to ADC thresholds of a transition area in accordance with calculating; and estimate core area and transition area according to the binary image and ADC thresholds of a core area in accordance with calculating; and process the core area obtained by estimating in accordance with high signal constraint processing according to DWI high signal thresholds of the core area in accordance with estimating, and obtaining the core and the transition area. The data analyzing module 240 is used to estimate the core area and the transition area, and calculate characteristic parameters of the estimated core area and the estimated transition area.

The inputting device 210 further includes data processing unit. The data processing unit is used to convert data of the DWI, the T2-weighted images and the ADC map to a lower bit data. An output end of the data processing unit is connected to the image processing module 220 and the brain tissue extracting module 230. The data of the T2-weighted image and the corresponding ADC map is 16-bit data. In order to calculate easily, the data of the T2-weighted image and the corresponding ADC map can be converted to 8-bit data or 4-bit data.

The image processing module 220 includes: a normal ADC values of obtaining module 221, an ADC low signal thresholds calculating and DWI high signal thresholds calculating module 222, a low signal constraint binarizing module 223, an estimating unit 224, a high signal constraint processing unit 225, a recovering unit 226, a second artifact removing unit 227, and a determination unit 228.

The normal ADC obtaining module 221 is connected to the brain tissue extracting module 230 and the inputting device 210, and is used to obtain ADC values of a normal brain tissue. The ADC low signal thresholds calculating and DWI high signal thresholds calculating module 222 is connected to the normal ADC values of obtaining module 221, and is used to calculate a product between the ADC of the normal brain tissue and a threshold coefficient, and obtain an ADC threshold of the core area and the transition area, and obtain a DWI high signal threshold of the core area. The low signal constraint binarizing module 223 is connected to the inputting device 210 and The ADC low signal thresholds calculating module 222, and is used to obtain a binary image based on binarizing the ADC map in accordance with ADC low signal constraint binarizing according to the ADC thresholds of the transition area. The estimating unit 224 is connected to the low signal constraint binarizing module 223 and the ADC low signal thresholds calculating module 224, and is used to estimate core area and transition area in accordance with the binary image.

The estimating unit 224 includes: a first unit and a first artifact removing unit. The first unit is configured to obtain a foreground connected area of each slice of the brain tissue in accordance with the binary image. The first artifact removing unit is configured to obtain a foreground area which is a part of the foreground connected area of which volume is greater than or equal to a first preset volume, to obtain a first image. The foreground connected area includes at least one voxel of which volume is no less than voxel of a second preset volume of which ADC value is less than the ADC threshold of the core area, the other part of the foreground connected area excluding the foreground area is the background area.

The high signal constraint processing unit 225 is connected to the estimating unit 224 and the DWI high signal thresholds calculating module 222, and is used to process the core area in accordance with high signal constraint processing according to ADC high signal thresholds of the core area in accordance with estimating, and select all voxels of brain tissue of which the DWI gray is no less than a constant, and denoting mean gray and standard deviation of the voxels for the DWI and the to AvgDWI(z) and SdDWI(z); denoting the high signal constraint of the DWI to DWITh(z), and calculate the high signal constraint of the DWI by the following formulas: DWITh(z)

=AvgDWI(z)+CC1*SdDWI(z), wherein CC1 represents a constant, * represents multiplication.

The recovering unit 226 is connected to the high signal constraint processing unit 225, and is used to set the voxel of which ADC value is no greater than the ADC threshold of the transition area as the foreground voxel, and find the adjacent voxels of each foreground voxel.

The second artifact removing unit 227 is connected to the recovering unit 226, and is used to set partial area of the foreground connected area of which volume is less than a preset volume as the background area, and finding the foreground connected area.

The determination unit 228 is connected to the second artifact removing unit 227, and is used to define an core area and an transition area in the first image, wherein the core area is a set of voxels of which ADC value is less than the ADC threshold of the core area, and the transition area is a set of voxels of which ADC value between the ADC threshold of the core area.

The characteristic parameter calculating unit 240 is connected to the determination unit 228, and is used to find at least one connected area having the largest voxels in the core area and the transition area, and calculate characteristic parameters of the core area and the transition area.

Embodiment 3

Thrombolysis Decision Guideline System

Figure 11:
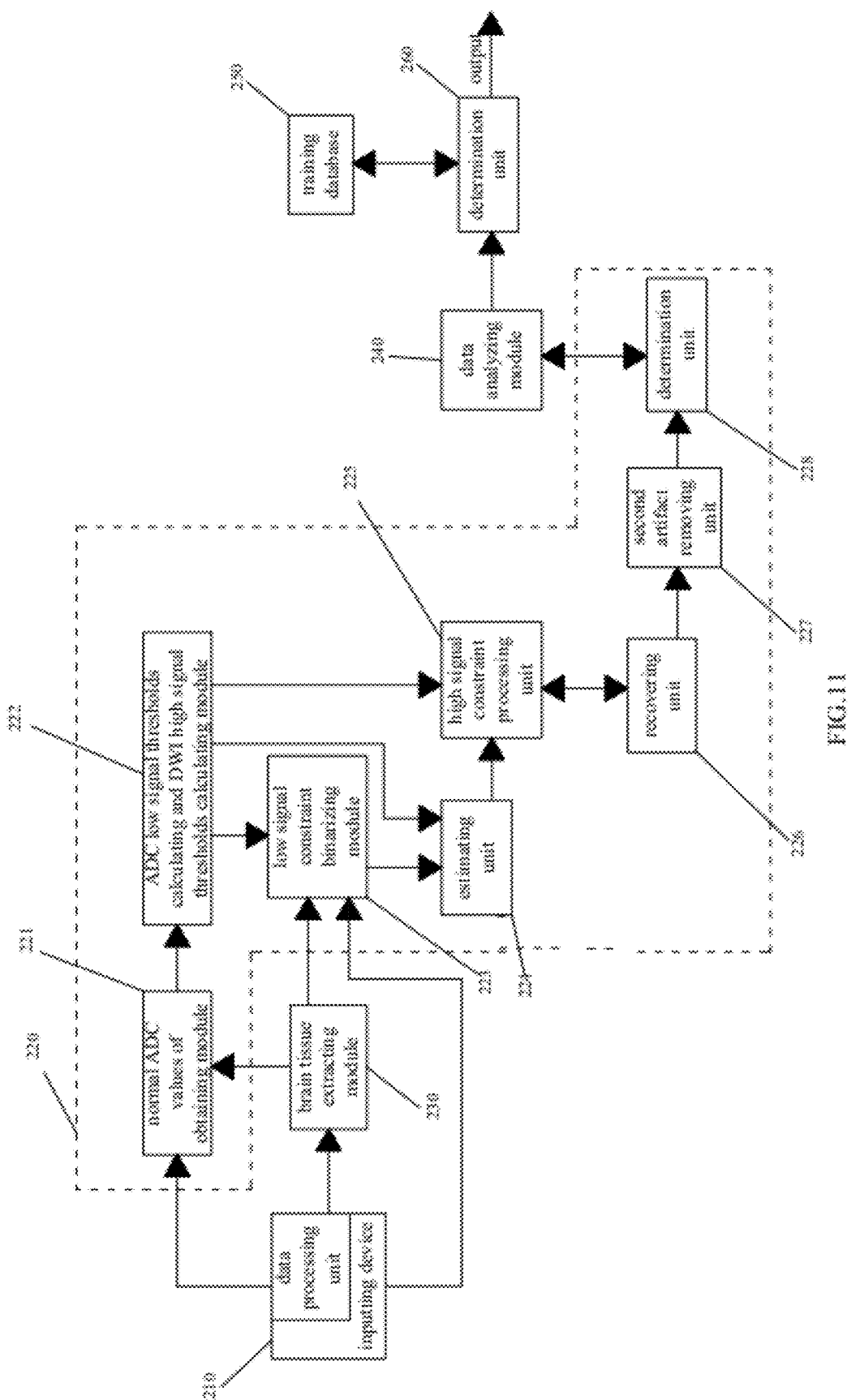
FIG. 11 is a block diagram of one embodiment of a thrombolysis decision guideline system.
Figure 12:
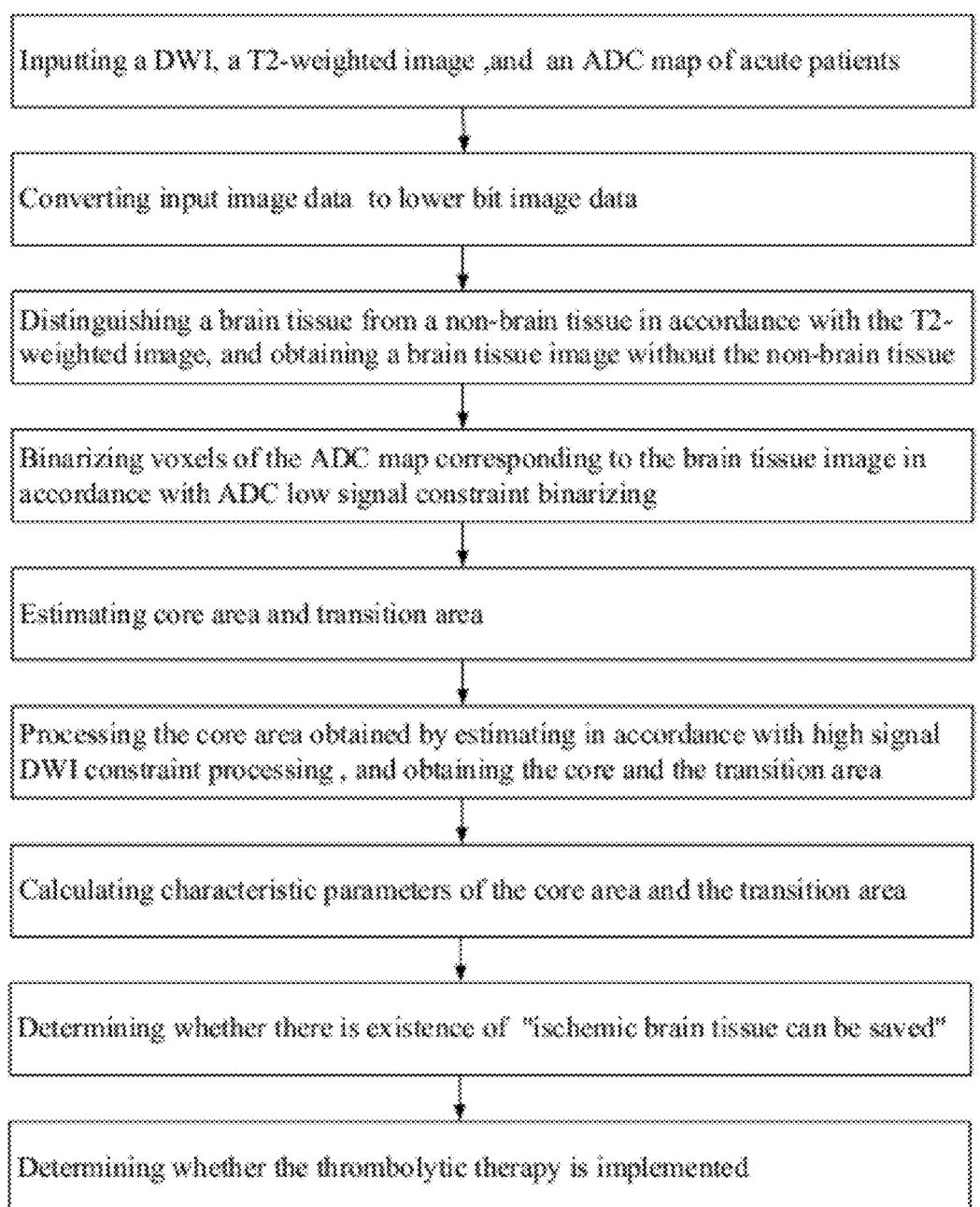
FIG. 12 is a flowchart of one embodiment of a method of thrombolysis decision guideline.

Based on the thrombolysis decision guideline system shown in FIG. 10, another thrombolysis decision guideline system further includes a training database 250 and determination unit 260, referring to FIG. 11 except the system architecture shown in FIG. 10. The training database 250 is used to store a preset threshold of the core area and the transition area. The determination unit 260 is used to compare output characteristic parameters of the characteristic parameters calculating unit to the preset threshold and output a comparison result.

The preset threshold of the training database includes a limiting value of total change of the ADC of the transition area, volume of the core area, and a variation coefficient of ADC of the core area.

The determination unit includes the first output unit, which is used to determine if the total change of ADC δADC of the transition area output by the characteristic parameter calculating unit is less than the threshold of the total change, or if volume volCore of the core area is greater than the threshold of the volume of the core area, if is, there is not "ischemic brain tissue can be saved"; if not, there is "ischemic brain tissue can be saved", and output the result. In one embodiment, the threshold of the total change equals 0.180, the threshold of the volume of the core area equals 100 mL The determination unit further includes the second output unit, which is used to determine if δAvgADC, δSdADC, δCvADC output from the characteristic parameter calculating unit is less than the preset threshold, and output the result.

The determination unit can also compare the follow parameters: CV1, CV2, δADC1, δADC2, volCore, volRatio, δAvgADC, δSdADC, δCvADC. For example, if δCvADC is less than 2 and there is "ischemic brain tissue can be saved", output of determination conclusion is recommending thrombolysis, wherein the output of determination conclusion can be report and image corresponded; if not, output of determination conclusion is not recommending thrombolysis.

It should be pointed that both the system for obtaining brain characteristic parameters and the thrombolysis decision guideline system can execute on separate computer systems.

Embodiment 4

Method of Thrombolysis Decision Guideline

Referring to FIG. 13, according to the method mentioned in the Embodiment 1, the brain image of patient are analyzed, and the characteristic parameters of the core area and the transition area are obtained. Two determination steps are needed to determine whether there is "ischemic brain tissue can be saved", and whether thrombolysis can be implemented.

In medicine, the "ischemic brain tissue can be saved" is determined by positron emission tomography (PET), and is approached by "unmatch" in clinical. The "unmatch" is determined by an abnormal volume of the PWI and the DWI. If the abnormal volume is greater than 1.2 times of volume of the DWI, there is "unmatch" which implies the existence of "ischemic brain tissue can be saved"; if not, there is no "unmatch".

In accordance with the above method, a set of training data needs to be established through the application and analysis in clinical or experiment, which is used to determine the three characteristic parameters threshold $\theta_{ADC}$, $\theta_r$, $\theta_{vol}$, corresponding to δADC, volRatio, volCore. For example, $\theta_{ADC}$=0.180, $\theta_{vol}$=100 ml, that is, when δADC<0.180 or volCore>100 ml, there is no "ischemic brain tissue can be saved"; otherwise, there is "ischemic brain tissue can be saved". Whether there is "ischemic brain tissue can be saved" should be determined by δADC or volCore.

After determining whether there is "ischemic brain tissue can be saved", the thrombolysis can be decided whether to implement. Similarly, a set of training data needs to be established through the application and analysis in clinical or experiment. The preset threshold of the training database includes the limiting value of a change of a mean ADC of partial edge area of the core area adjacent to the transition area δAvgADC, a change of the mean square errors of ADC of partial edge area of the core area adjacent to the transition area δSdADC, and a change of the variation coefficient of ADC of partial edge area of the core area adjacent to the transition area δCvADC. The general indication of thrombolysis is determined by the set of training data which includes: the gradient of ADC the transition area, the radial distance of the transition area, the total change of ADC of the transition area, the mean ADC value of the core area, the variation coefficient of ADC of the core area, volume of the core area, the volume ratio, the change of a mean ADC of partial edge area of the core area adjacent to the transition area, the change of the mean square errors of ADC of partial edge area of the core area adjacent to the transition area, and the change of the variation coefficient of ADC of partial edge area of the core area adjacent to the transition area. In other words, the general indication of thrombolysis depends on the limitation or range of the parameters mentioned before, the threshold or the range can be obtained by a established set of training data, and is used for the general indication of thrombolysis.

According to the above data has been validated, δADC is mainly based parameter, VolCore, VolTR, δAvgADC, δSdADC, and δCvADC are complemented parameters to determine whether the thrombolysis can be implemented. Firstly, whether there is "ischemic brain tissue can be saved" is determined by the total change of ADC of the transition area and the volume of the core area, if there is not "ischemic brain tissue can be saved", thrombolysis can not be implemented; if there is, indication of thrombolysis is determined by whether the change of variation coefficient of ADC of core area is less than the preset threshold.

In summary, 16-bit data of the T2-weighted image, the DWI and the ADC map are converted a lower bit data, such that speed and accuracy of processing of the present disclosure are improved. Secondly, the present invention by ADC map and DWI to strike a brain tissue to limit the computational domain. Secondly, the present invention calculates the patient's ADC values of normal brain tissue to exclude the impact of different individuals, binarizates the ADC map by low signal constraints, and estimates the core area and the transition area by characteristics of the core area with high DWI, and finally selects connected area in the core the core area and the transition area in two axial slices with the most voxels to calculate the characteristic parameters, in such doing, ensure the representativeness, but also avoid to handle areas due to artifacts. Analysised characteristic parameters include: the radial distance of the transition area, the gradient of ADC the transition area, the total change of radial ADC of the transition area, volume of the transition, and volume of the core area. Whether there is "ischemic brain tissue can be saved" is determined by the characteristic parameters in clinical, and image characteristics of the "ischemic brain tissue can be saved" is analysed by computer. The image characteristics include: the mean ADC value of the core area, variation coefficient of ADC of the core area, volume of the core area, volume ratio of the transition area and the core area, the change of a mean ADC of partial edge area of the core area adjacent to the transition area δAvgADC, the change of the mean square errors of ADC of partial edge area of the core area adjacent to the transition area δSdADC, and the change of the variation coefficient of ADC of partial edge area of the core area adjacent to the transition area δCvADC, in order to provide the middle of the reference data of whether thrombolysis is recommended for clinical use.

Comparing to the clinical programs of DWI and PWI, the present disclosure has the following advantages:

The PWI can also be omitted, and the degree of functional characterization of perfusion abnormalities is reflected without the PWI. Therefore, cost and time of treatment of patient can be saved.

In addition, the thrombolysis whether is implemented can be determined more accurately. Therefore, suffering and economic burden of the patient can be reduced.

Although the present disclosure has been described with reference to the embodiments thereof and the best modes for carrying out the present disclosure, it is apparent to those skilled in the art that a variety of modifications and changes may be made without departing from the scope of the present disclosure, which is intended to be defined by the appended claims.

What is claimed is:

1. A method for obtaining brain characteristic parameters, comprising:
   step S1, selecting a magnetic resonance perfusion weighted imaging of a patient obtained in accordance with magnetic resonance, wherein the magnetic resonance perfusion weighted imaging comprises a diffusion-weighted image, a T2-weighted image, and an apparent diffusion coefficient (ADC) map;
   step S2, distinguishing a brain tissue from a non-brain tissue in accordance with the T2-weighted image, and obtaining a brain tissue image without the non-brain tissue;
   step S3, processing voxels of the ADC map corresponding to the brain tissue image in accordance with low ADC signal constraint binarizing to obtain a binary image according to calculated ADC thresholds of a transition area;
   step S4, estimating a core area and the transition area according to the binary image and calculated ADC thresholds of the core area;
   step S5, processing the estimated core area according to high signal constraint processing in accordance with high thresholds of the diffusion-weighted image of the estimated core area, and obtaining the core area and the transition area; and
   step S6, calculating characteristic parameters of the core area and the transition area.

2. The method for obtaining brain characteristic parameters of claim 1, further comprising step S11, converting input image data of the diffusion-weighted image to lower bit image data, between step S1 and step S2.

3. The method for obtaining brain characteristic parameters of claim 1, wherein step S2 comprises:
   step S21, obtaining a low signal threshold of the brain tissue by dividing the T2-weighted image into I-IV class having gray scale values from low to high by fuzzy C-means clustering;
   step S22, binarizating the T2-weighted image in accordance with the low signal threshold to obtain the binary image; if gray scale of one pixel of the T2-weighted image is no less than the low signal threshold, set the pixel to foreground; if not, set the pixel to background;
   step S23, obtaining the largest connected area of the binary image; and
   step S24, opening slices of the largest connected area in the mathematical morphology, determining the biggest foreground connected area and obtaining a brain image by filling in the slices of the largest connected area.

4. The method for obtaining brain characteristic parameters of claim 3, wherein step S3 and step S4 comprise:
   step S31, determining an ADC value of normal brain tissue of the brain tissue image based on the ADC map; and
   step S32, calculating a product between the ADC value of the normal brain tissue and a threshold coefficient, and obtaining ADC threshold of the core area and ADC threshold of the transition area.

5. The method for obtaining brain characteristic parameters of claim 4, wherein step S31 comprises:
   step S311, counting occurrence times of each ADC value of the ADC map corresponding to the brain tissue image; and
   step S312, determining the ADC value of the normal brain tissue by the counting result, wherein the ADC value of the normal brain tissue is any value in neighborhood scope of the ADC value of the highest occurrence times.

6. The method for obtaining brain characteristic parameters of claim 5, wherein the ADC value of the normal brain tissue is any value in neighborhood scope of the most frequent of ADC values in step S31; the ADC thresholds of the core area and the ADC thresholds the transition area are calculated based on the ADC value of the normal brain tissue in step S32; each slice of the brain tissue image is binarized based on the ADC thresholds of the transition area in step S3; the core area and the transition area are estimated based on the binary image of the each slice in step S4; the core area and the transition area are obtained by high signal constraint processing of the binary image of the each slice in step S5; characteristic parameters of the core area and the transition area is calculated in step S6.

7. The method for obtaining brain characteristic parameters of claim 4, wherein step S4 comprises:
step S41, obtaining a foreground connected area in accordance with the binary image of the ADC map; and
step S42, dividing the foreground connected area into a foreground area and a background area to obtain a first image, wherein if a volume of the foreground connected area is not less than a first pre-volume, and a voxel of the foreground connected area of which ADC value is less than the ADC threshold of the core area is not less than a second pre-volume, the foreground connected area is a foreground; if not, the foreground connected area is a background.

8. The method for obtaining brain characteristic parameters of claim 7, wherein step S5 comprises:
denoting the mean gray scale value of the diffusion-weighted image of the core area to DWIAvgF;
denoting the diffusion-weighted image gray scale value of all voxels adjacent to the core area to DWIAvgB;
selecting all voxels of brain tissue of which the diffusion-weighted image gray scale value is no less than a constant, and denoting mean gray scale and standard deviation of the voxels for the diffusion-weighted image to AvgDWI(z) and SdDWI(z);
denoting the high signal constraint of the diffusion-weighted image to DWITh(z), and calculating the high signal threshold of the diffusion-weighted image by the following formulas:

$$DWITh(z)=avgDWI(z)+CC1*SdDWI(z),$$

wherein DWITh(z) represents the high signal threshold of the diffusion-weighted image, AvgDWI(z) represents the mean gray scale of voxels in the diffusion-weighted image, SdDWI(z) represents the standard deviation of voxels in the diffusion-weighted image, CC1 represents a constant, * represents multiplication; and
wherein if (DWIAvgF−DWIAvgB)>CC2 or (DWIAvgF−DWITh(z))>CC3, the core area and the transition area are retained; if not, the core area and the transition area are background; wherein CC2 and CC3 represent constants.

9. The method for obtaining brain characteristic parameters of claim 8, wherein CC1 is a range from about 1.1 to about 1.5, CC2 is a range from about 10 to about 20, and CC3 is a range from about 4 to about 8.

10. The method for obtaining brain characteristic parameters of claim 8, wherein the method further comprises:
a recovering step between step S5 and step S6, and the recovering step comprising: setting the voxel of which ADC value is no greater than the ADC threshold of the transition area as the foreground voxel, and finding the adjacent voxels of each foreground voxel of the first image.

11. The method for obtaining brain characteristic parameters of claim 10, wherein the method further comprises:
a second artifact removing step between the recovering step and step S6, and the second artifact removing step comprising: setting partial area of the foreground connected area of which volume is less than a preset volume as the background area, and finding the foreground connected area of the first image.

12. The method for obtaining brain characteristic parameters of claim 7, wherein step S6 comprises:
defining the core area as a set of voxels of which ADC value is less than the ADC threshold of the core area, and the transition area as a set of voxels of which ADC value between the ADC threshold of the core area and the ADC threshold of the transition area; finding at least one connected area having the most foreground voxel of the core area and the transition area, and calculating characteristic parameters of the core area and the transition area in accordance with the connected area.

13. The method for obtaining brain characteristic parameters of claim 12, wherein step S6 comprises:
step S61, calculating an ADC value gradient of the transition area, wherein step S61 comprises:
step S611, finding a connected area having the largest foreground voxels;
step S612, finding interior points of the connected area;
step S613, calculating a mean ADC value gradient of interior points of which ADC value between the ADC threshold of the core area and the ADC threshold of the transition area;
step S614, calculating a mean ADC value of voxels of which ADC value between the ADC threshold of the core area and the ADC threshold of the transition area; and
step S615, calculating an ADC value gradient of the transition area by the following formula:

$$\text{gradAvgN}=\text{gradAvg} \times C/(\text{ADC}_{ref} \times \text{avgADC});$$

wherein gradAvgN represents the ADC value gradient of the transition area, gradAvg represents the mean ADC value gradient of the connected area in step S613, C represents a positive constant, $ADC_{ref}$ represents ADC value of the normal brain tissue, and avgADC represents the mean ADC value gradient in step S614;
step S62, calculating a radial distance of the transition area, wherein step S62 comprises:
step S621, calculating the number of first voxels of the connected area of which ADC value is less than the ADC threshold of the core area, and the number of second voxels of the connected area of which ADC value between the ADC threshold of the core area and the ADC threshold of the transition area;
step S622, calculating a radius of the core area of the connected area and a radius of the core area and the transition area of the connected area respectively, wherein the radius of the core area is square root of a quotient which is calculated by dividing the number of the first voxels to pi and the radius of the transition area is square root of a quotient which is calculated by dividing the sum of the number of the first voxels and the number of the second voxels to pi; and
step S623, calculating a radial distance of the transition area by subtracting the radius of the core area and the radius of the transition area.

14. The method for obtaining brain characteristic parameters of claim 13, wherein step S6 further comprises step S63: calculating a total change of radial ADC value of the transition area by the following formulas:

$$\delta ADC = \text{gradAvgN} \times \delta R/ADC_{ref};$$

wherein δADC is a total change of ADC, gradAvgN represents the gradient of ADC value of the transition area, δR represents the radial distance of the transition area, and $ADC_{ref}$ represents ADC value of the normal brain tissue.

15. The method for obtaining brain characteristic parameters of claim 12, wherein step S6 further comprises step S64: calculating a variation coefficient of ADC value of the core area; wherein step S64 comprises:

step S641, calculating a mean ADC value and a mean square errors of voxels of which ADC value is less than the ADC threshold of the core area;

step S642, dividing the mean ADC value by the mean square errors, and the variation coefficient of ADC value of the connected area is equal to the quotient.

16. The method for obtaining brain characteristic parameters of claim 12, wherein step S6 further comprises:

step S65, calculating parameters of partial edge area of the core area adjacent to the transition area and a mean ADC value of voxels of all core area and a mean square errors of voxels of all core area, and denoting the mean ADC value and the mean square errors to $AvgADC_{core}$ and $SdADC_{core}$; eroding the core area by 3×3 mathematical morphology erosion, and denoting a mean ADC value and a mean square errors of the remaining core area to AvgADCcoreE and $SdADC_{coreE}$;

calculating the change of the mean ADC value of partial edge area of the core area adjacent to the transition area by the following formulas:

$$\delta AvgADC = (AvgADC_{core} - AvgADC_{coreE})/AvgADC_{core};$$

calculating the change of the mean square errors of ADC value of partial edge area of the core area adjacent to the transition area by the following formulas:

$$\delta SdADC = (SdADC_{core} - SdADC_{coreE})/SdADC_{core};$$

calculating the change of the variation coefficient of ADC value of partial edge area of the core area adjacent to the transition area by the following formulas:

$$\delta CvADC = \delta SdADC/\delta AvgADC.$$

17. The method for obtaining brain characteristic parameters of claim 12, wherein step S6 further comprises: selecting a first and second connected area and obtaining characteristic parameters of the first and second connected area; comparing the characteristic parameters of the first connected area to that of the second connected area, and outputting the minimum characteristic parameters or the maximum characteristic parameters.

18. The method for obtaining brain characteristic parameters of claim 1, wherein step S3 further comprises: if an ADC value of a pixel is greater than the ADC threshold of the transition area, the pixel is a background pixel; if not, the pixel is a foreground pixel.

19. A system for obtaining brain characteristic parameters, comprising:

an inputting device, configured to obtain a magnetic resonance perfusion weighted imaging of a patient obtained in accordance with magnetic resonance, wherein the magnetic resonance perfusion weighted imaging comprises a diffusion-weighted image, a T2-weighted image, and an apparent diffusion coefficient (ADC) map;

a brain tissue extracting module, configured to calculate a brain tissue of patient in accordance with the T2-weighted image, and output a brain image;

an image processing module, configured to obtain a binary image based on binarizing the voxels of the ADC map corresponding to the brain tissue image in accordance with low ADC signal constraint binarizing according to ADC thresholds of a transition area in accordance with calculating; and estimate core area and transition area according to the binary image and ADC thresholds of a core area in accordance with calculating; and process the core area obtained by estimating in accordance with high signal constraint processing according to diffusion-weighted image high signal thresholds of the core area in accordance with estimating, and obtaining the core and the transition area; and a characteristic parameters calculating unit, configured to calculate characteristic parameters of the core area and the transition area.

20. The system for obtaining brain characteristic parameters of claim 19, wherein the inputting device comprises a data processing unit configured to convert data of the DWI, the T2-weighted image, and the ADC map to a lower bit data, wherein an output end of the data processing unit is connected to the image processing module and the brain tissue extracting module.

21. The system for obtaining brain characteristic parameters of claim 19, wherein the image processing module comprises:

a normal ADC value obtaining module, configured to obtain ADC values of a normal brain tissue, wherein the normal ADC values of obtaining module is connected to the brain tissue extracting module and the outputting device;

an ADC low signal thresholds calculating module, configured to calculate a product between the ADC value of the normal brain tissue and a threshold coefficient, and obtain an ADC threshold of the core area and the transition area;

a diffusion-weighted image high signal thresholds calculating module, configured to select all voxels of brain tissue of which the diffusion-weighted image gray scale is no less than a constant, and denoting mean gray scale and standard deviation of the voxels for the diffusion-weighted image to AvgDWI(z) and SdDWI(z); denoting the high signal threshold of the diffusion-weighted image to DWITh(z), and calculate the high signal constraint of the DWI by the following formulas:

$$DWITh(z) = AvgDWI(z) + CC1 * SdDWI(z), \text{ wherein } CC1$$
represents a constant, * represents multiplication;

a low signal constraint binarizing module, configured to obtain a binary image based on binarizing the ADC map in accordance with ADC low signal constraint binarizing according to the ADC thresholds of the transition area, wherein the low signal constraint binarizing module is connected to the inputting device, the brain tissue extracting module and the ADC low signal thresholds calculating module;

an estimating unit, configured to estimate core area and transition area in accordance with the binary image, wherein the estimating unit is connected to the low signal constraint binarizing module and the ADC low signal thresholds calculating module; and a high signal constraint processing unit, configured to process the core area in accordance with high signal constraint processing according to ADC high signal thresholds of the core area in accordance with estimating, wherein the high signal constraint processing unit is connected to the estimating unit and the diffusion-weighted image high signal thresholds calculating module;

a determination unit, configured to define an core area and an transition area, wherein the core area is a set of voxels of which ADC value is less than the ADC threshold of the core area, and the transition area is a set of voxels of which ADC value between the ADC threshold of the core area; and a characteristic parameter calculating unit, configured to find at least one connected area having the largest voxels in the core area and the transition area, and calculate characteristic parameters of the core area and the transition area, wherein the characteristic parameter calculating unit is connected to the determination unit.

22. The system for obtaining brain characteristic parameters of claim 21, wherein the high signal constraint processing unit is configured to:
denote the mean gray scale of the diffusion-weighted image of the core area to DW1AvgF;
denote the diffusion-weighted image gray scale of all voxels adjacent to the core area to DWIAvgB; and
denote the high signal threshold of the diffusion-weighted image to DW1Th(z);
wherein if (DWIAvgF−DW1AvgB)>CC2 or (DW1AvgF−DW1Th(z))>CC3, the core area and the transition area is retained; if not, the core area and the transition area is background; wherein CC2 and CC3 represent constants.

23. The system for obtaining brain characteristic parameters of claim 21, wherein the estimating unit comprises:
a first unit, configured to obtain a foreground connected area of each slice of the brain tissue in accordance with the binary image;
a first artifact removing unit, configured to obtain a foreground area, the foreground area is a part of the foreground connected area of which volume is greater than or equal to a first preset volume, and comprises at least one voxel of which volume is greater than or equal to a second preset volume, and of which ADC value is less than the ADC threshold of the core area, the other part of the foreground connected area excluding the foreground area is the background area.

24. The system for obtaining brain characteristic parameters of claim 21, wherein the image processing module further comprises:
a recovering unit, configured to set the voxel of which ADC value is no greater than the ADC threshold of the transition area as the foreground voxel, and find the adjacent voxels of each foreground voxel, wherein the recovering unit is connected between the high signal constraint processing unit and the determination unit.

25. The system for obtaining brain characteristic parameters of claim 24, wherein the image processing module further comprises:
a second artifact removing unit, configured to set partial area of the foreground connected area of which volume is less than a preset volume as the background area, and finding the foreground connected area, wherein the second artifact removing unit is connected between the recovering unit and the determination unit.

26. A thrombolysis decision guideline system, comprising:
an inputting device, configured to obtain a magnetic resonance perfusion weighted imaging of a patient obtained in accordance with magnetic resonance, wherein the magnetic resonance perfusion weighted imaging comprises a diffusion-weighted image, a T2-weighted image, and an apparent diffusion coefficient (ADC) map;
a brain tissue extracting module, configured to calculate a brain tissue of patient in accordance with the T2-weighted image, and output a brain image;
an image processing module, configured to obtain a binary image based on binarizing the voxels of the ADC map corresponding to the brain tissue image in accordance with ADC low signal constraint binarizing according to ADC thresholds of a transition area in accordance with calculating; and estimate core area and transition area according to the binary image and ADC thresholds of a core area in accordance with calculating; and process the core area obtained by estimating in accordance with high signal constraint processing according to diffusion-weighted image high signal thresholds of the core area in accordance with estimating, and obtaining the core and the transition area;
a characteristic parameters calculating unit, configured to calculate characteristic parameters of the core area and the transition area;
a training database, configured to store a preset threshold of the core area and the transition area; and
a determination unit, configured to compare output characteristic parameters of the characteristic parameters calculating unit to the preset threshold and output a comparison result.

27. The thrombolysis decision guideline system of claim 26, wherein the preset threshold of the training database comprises a limiting value of variation coefficient of ADC value of the core area, a total change of radial ADC value gradient of the transition area, volume of the core area, volume ratio of the core area and the transition area, a mean ADC value of partial edge area of the core area adjacent to the transition area, a change of the mean square errors of ADC value, and a change of the variation coefficient of ADC value.

28. A method of thrombolysis decision, comprising:
step S1, selecting a magnetic resonance perfusion weighted imaging of a patient obtained in accordance with magnetic resonance, wherein the magnetic resonance perfusion weighted imaging comprises a diffusion-weighted image, a T2-weighted image, and an apparent diffusion coefficient (ADC) map;
step S2, distinguishing a brain tissue from a non-brain tissue in accordance with the T2-weighted image, and obtaining a brain tissue image without the non-brain tissue;
step S3, binarizing voxels of the ADC map corresponding to the brain tissue image in accordance with ADC low signal constraint binarizing to obtain a binary image according to ADC thresholds of a transition area in accordance with calculating;
step S4, estimating core area and transition area according to the binary image and ADC thresholds of the core area in accordance with calculating;
step S5, processing the core area obtained by estimating in accordance with high signal constraint processing according to diffusion-weighted image high signal thresholds of the core area in accordance with estimating, and obtaining the core and the transition area;
step S6, calculating characteristic parameters of the core area and the transition area; and
step S7, comparing output characteristic parameters to a preset threshold and output a comparison result.

29. The method of thrombolysis decision of claim 28, wherein step S7 comprises: obtaining the preset threshold based on comparing and training at least one parameter of a radial distance of the transition area, an ADC value gradient of the transition area, a total change of ADC value gradient of the transition area, a mean ADC value of the core area, a variation coefficient of ADC value of the core area, volume of the core area, volume ratio of the core area and the transition area, a mean ADC value of partial edge area of the core area adjacent to the transition area, a change of the mean square errors of ADC value, and a change of the variation coefficient of ADC value.

* * * * *